United States Patent
Sabesan

(10) Patent No.: US 9,681,836 B2
(45) Date of Patent: Jun. 20, 2017

(54) METHODS, SYSTEMS AND APPARATUSES FOR DETECTING SEIZURE AND NON-SEIZURE STATES

(75) Inventor: Shivkumar Sabesan, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 663 days.

(21) Appl. No.: 13/557,351

(22) Filed: Jul. 25, 2012

(65) Prior Publication Data

US 2014/0031635 A1 Jan. 30, 2014

(51) Int. Cl.
*G01N 33/50* (2006.01)
*A61B 5/00* (2006.01)
*A61B 5/11* (2006.01)
*A61B 5/0402* (2006.01)
*A61B 5/053* (2006.01)
*A61B 5/08* (2006.01)

(52) U.S. Cl.
CPC .............. *A61B 5/4094* (2013.01); *A61B 5/11* (2013.01); *A61B 5/7253* (2013.01); *A61B 5/7282* (2013.01); *A61B 5/0402* (2013.01); *A61B 5/0531* (2013.01); *A61B 5/08* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 4,197,856 A | 4/1980 | Northrop | |
| RE30,530 E | 2/1981 | Hopwood | |
| 4,320,766 A | 3/1982 | Alihanka et al. | |
| 5,062,169 A | 11/1991 | Kennedy et al. | |
| 5,090,410 A | 2/1992 | Saper et al. | |
| 5,168,874 A | 12/1992 | Segalowitz | |
| 5,194,847 A | 3/1993 | Taylor et al. | |
| 5,213,568 A | 5/1993 | Lattin et al. | |
| 5,304,206 A | 4/1994 | Baker, Jr. et al. | |
| 5,335,657 A | 8/1994 | Terry, Jr. et al. | |
| 5,349,962 A | 9/1994 | Lockard et al. | |
| 5,423,325 A | 6/1995 | Burton | |
| 5,503,159 A | 4/1996 | Burton | |
| 5,511,553 A | 4/1996 | Segalowitz | |
| 5,513,649 A | 5/1996 | Gevins et al. | |
| 5,523,742 A | 6/1996 | Simkins et al. | |
| 5,549,650 A | 8/1996 | Bornzin et al. | |
| 5,610,590 A | 3/1997 | Johnson et al. | |
| 5,645,077 A | 7/1997 | Foxlin | |
| 5,702,323 A | 12/1997 | Poulton | |
| 5,748,113 A | 5/1998 | Torch | |
| 5,807,284 A | 9/1998 | Foxlin | |
| 5,808,552 A | 9/1998 | Wiley et al. | |
| 5,810,722 A | 9/1998 | Heikkila | |
| 5,853,005 A | 12/1998 | Scanlon | |
| 5,876,350 A | 3/1999 | Lo et al. | |
| 5,879,309 A | 3/1999 | Johnson et al. | |
| 5,905,436 A | 5/1999 | Dwight et al. | |
| 5,916,181 A | 6/1999 | Socci et al. | |
| 5,978,972 A | 11/1999 | Stewart et al. | |
| 6,009,349 A | 12/1999 | Mouchawar et al. | |
| 6,048,324 A | 4/2000 | Socci et al. | |
| 6,052,619 A | 4/2000 | John | |
| 6,058,328 A | 5/2000 | Levine et al. | |
| 6,066,075 A | 5/2000 | Poulton | |
| 6,095,991 A | 8/2000 | Krausman et al. | |
| 6,104,947 A | 8/2000 | Heikkila et al. | |
| 6,134,474 A | 10/2000 | Fischell et al. | |
| 6,162,191 A | 12/2000 | Foxlin | |
| 6,163,281 A | 12/2000 | Torch | |
| 6,216,537 B1 | 4/2001 | Henschel et al. | |
| 6,246,344 B1 | 6/2001 | Torch | |
| 6,277,080 B1 | 8/2001 | Nissilä et al. | |
| 6,315,719 B1 | 11/2001 | Rode et al. | |
| 6,315,740 B1 | 11/2001 | Singh | |
| 6,356,784 B1 | 3/2002 | Lozano et al. | |
| 6,361,507 B1 | 3/2002 | Foxlin | |
| 6,361,508 B1 | 3/2002 | Johnson et al. | |
| 6,377,845 B1 | 4/2002 | Kinast | |
| 6,385,486 B1 | 5/2002 | John et al. | |
| 6,405,077 B1 | 6/2002 | Birnbaum et al. | |
| 6,411,841 B2 | 6/2002 | Heikkilä | |
| 6,416,471 B1 | 7/2002 | Kumar et al. | |
| 6,428,476 B1 | 8/2002 | Heikkilä et al. | |

(Continued)

OTHER PUBLICATIONS

Pardalos, Nonlinear Dynamical Systems and Adaptive Filters in Biomedicine, 2003, Annals of Operations Research, No. 119, pp. 119-142.*

(Continued)

*Primary Examiner* — Jason Sims

(74) *Attorney, Agent, or Firm* — Foley & Lardner LLP

(57) ABSTRACT

Methods, systems, and apparatuses for detecting seizure events are disclosed, having at least one accelerometer to be positioned on a patient and configured to collect acceleration data and a processor in communication with the at least one accelerometer and configured to receive acceleration data from the at least one accelerometer. The processor may apply at least one non-linear operator to the acceleration data to determine whether the acceleration data indicates an event, such application including calculation of a non-linear energy of the acceleration data and performance of at least one secondary analysis to determine whether the event is a seizure.

26 Claims, 12 Drawing Sheets

(56) References Cited

U.S. PATENT DOCUMENTS

| | | |
|---|---|---|
| 6,441,731 B1 | 8/2002 | Hess |
| 6,454,708 B1 | 9/2002 | Ferguson et al. |
| 6,463,328 B1 | 10/2002 | John |
| 6,466,820 B1 | 10/2002 | Juran et al. |
| 6,495,601 B1 | 12/2002 | Hochman |
| 6,496,705 B1 | 12/2002 | Ng et al. |
| 6,537,227 B2 | 3/2003 | Kinnunen et al. |
| 6,539,263 B1 | 3/2003 | Schiff et al. |
| 6,540,686 B2 | 4/2003 | Heikkilä et al. |
| 6,542,081 B2 | 4/2003 | Torch |
| 6,605,044 B2 | 8/2003 | Bimbaum |
| 6,611,783 B2 | 8/2003 | Kelly, Jr. et al. |
| 6,622,038 B2 | 9/2003 | Barrett et al. |
| 6,622,041 B2 | 9/2003 | Terry, Jr. et al. |
| 6,629,990 B2 | 10/2003 | Putz et al. |
| 6,644,321 B1 | 11/2003 | Behm |
| 6,652,478 B1 | 11/2003 | Gartstein et al. |
| 6,687,535 B2 | 2/2004 | Hautala et al. |
| 6,730,047 B2 | 5/2004 | Socci et al. |
| 6,763,256 B2 | 7/2004 | Kimball et al. |
| 6,786,877 B2 | 9/2004 | Foxlin |
| 6,793,670 B2 | 9/2004 | Osorio et al. |
| 6,804,558 B2 | 10/2004 | Haller et al. |
| 6,808,473 B2 | 10/2004 | Hisano et al. |
| 6,819,956 B2 | 11/2004 | DiLorenzo |
| 6,847,892 B2 | 1/2005 | Zhou et al. |
| 6,850,601 B2 | 2/2005 | Jones, III et al. |
| 6,879,850 B2 | 4/2005 | Kimball |
| 6,923,784 B2 | 8/2005 | Stein |
| 6,931,274 B2 | 8/2005 | Williams |
| 6,931,277 B1 | 8/2005 | Yuzhakov et al. |
| 6,980,852 B2 | 12/2005 | Jersey-Willuhn et al. |
| 6,984,993 B2 | 1/2006 | Ariav |
| 7,024,247 B2 | 4/2006 | Gliner et al. |
| 7,034,008 B2 | 4/2006 | Donahue et al. |
| 7,035,684 B2 | 4/2006 | Lee |
| 7,057,053 B2 | 6/2006 | Beatch et al. |
| 7,062,313 B2 | 6/2006 | Nissilä |
| 7,068,842 B2 | 6/2006 | Liang et al. |
| 7,077,810 B2 | 7/2006 | Lange et al. |
| 7,101,877 B2 | 9/2006 | Bain et al. |
| 7,104,947 B2 | 9/2006 | Riehl |
| 7,110,820 B2 | 9/2006 | Tcheng et al. |
| 7,112,319 B2 | 9/2006 | Broderick et al. |
| 7,127,370 B2 | 10/2006 | Kelly, Jr. et al. |
| 7,146,211 B2 | 12/2006 | Frei et al. |
| 7,146,218 B2 | 12/2006 | Esteller et al. |
| 7,149,773 B2 | 12/2006 | Haller et al. |
| 7,167,743 B2 | 1/2007 | Heruth et al. |
| 7,169,107 B2 | 1/2007 | Jersey-Willuhn et al. |
| 7,177,678 B1 | 2/2007 | Osorio et al. |
| 7,181,505 B2 | 2/2007 | Haller et al. |
| 7,184,820 B2 | 2/2007 | Jersey-Willuhn et al. |
| 7,200,439 B2 | 4/2007 | Zdeblick et al. |
| 7,203,548 B2 | 4/2007 | Whitehurst et al. |
| 7,206,630 B1 | 4/2007 | Tarler |
| 7,209,787 B2 | 4/2007 | DiLorenzo |
| 7,244,769 B2 | 7/2007 | Epstein et al. |
| 7,257,438 B2 | 8/2007 | Kinast |
| 7,259,184 B2 | 8/2007 | Beatch et al. |
| 7,274,298 B2 | 9/2007 | Frank |
| 7,285,090 B2 | 10/2007 | Stivoric et al. |
| 7,289,850 B2 | 10/2007 | Burnes et al. |
| 7,292,890 B2 | 11/2007 | Whitehurst et al. |
| 7,304,580 B2 | 12/2007 | Sullivan et al. |
| 7,313,440 B2 | 12/2007 | Miesel |
| 7,314,451 B2 | 1/2008 | Halperin et al. |
| 7,330,760 B2 | 2/2008 | Heruth et al. |
| 7,361,141 B2 | 4/2008 | Nissila et al. |
| 7,376,463 B2 | 5/2008 | Salo et al. |
| 7,385,443 B1 | 6/2008 | Denison |
| 7,387,607 B2 | 6/2008 | Holt et al. |
| 7,389,147 B2 | 6/2008 | Wahlstrand et al. |
| 7,395,113 B2 | 7/2008 | Heruth et al. |
| 7,396,330 B2 | 7/2008 | Banet et al. |
| 7,416,541 B2 | 8/2008 | Yuzhakov et al. |
| 7,418,292 B2 | 8/2008 | Shafer |
| 7,420,472 B2 | 9/2008 | Tran |
| 7,447,545 B2 | 11/2008 | Heruth et al. |
| 7,454,245 B2 | 11/2008 | Armstrong et al. |
| 7,477,934 B2 | 1/2009 | Nissilä et al. |
| 7,488,293 B2 | 2/2009 | Marcovecchio et al. |
| 7,488,294 B2 | 2/2009 | Torch |
| 7,491,181 B2 | 2/2009 | Heruth et al. |
| 7,494,464 B2 | 2/2009 | Rzesnitzek et al. |
| 7,499,742 B2 | 3/2009 | Bolea et al. |
| 7,502,643 B2 | 3/2009 | Farringdon et al. |
| 7,515,054 B2 | 4/2009 | Torch |
| 7,517,328 B2 | 4/2009 | Hoffmann |
| 7,524,879 B2 | 4/2009 | Beatch et al. |
| 7,534,790 B2 | 5/2009 | Bain et al. |
| 7,539,532 B2 | 5/2009 | Tran |
| 7,539,533 B2 | 5/2009 | Tran |
| 7,539,543 B2 | 5/2009 | Schiff et al. |
| 7,542,807 B2 | 6/2009 | Bertolero et al. |
| 7,542,878 B2 | 6/2009 | Nanikashvili |
| 7,558,622 B2 | 7/2009 | Tran |
| 7,565,132 B2 | 7/2009 | Ben Ayed |
| 7,585,839 B2 | 9/2009 | Larsen et al. |
| 7,590,453 B2 | 9/2009 | Heruth et al. |
| 7,619,005 B2 | 11/2009 | Epstein et al. |
| 7,620,456 B2 | 11/2009 | Gliner et al. |
| 7,629,890 B2 | 12/2009 | Sullivan et al. |
| 7,643,655 B2 | 1/2010 | Liang et al. |
| 7,647,121 B2 | 1/2010 | Wahlstrand et al. |
| 7,654,957 B2 | 2/2010 | Abreu |
| 7,658,112 B2 | 2/2010 | Nakamura |
| 7,662,105 B2 | 2/2010 | Hatlestad |
| 7,666,121 B2 | 2/2010 | Zhou |
| 7,668,588 B2 | 2/2010 | Kovacs |
| 7,676,269 B2 | 3/2010 | Yun et al. |
| 7,684,854 B2 | 3/2010 | Park et al. |
| 7,714,757 B2 | 5/2010 | Denison et al. |
| 7,717,848 B2 | 5/2010 | Heruth et al. |
| 7,720,547 B2 | 5/2010 | Denker et al. |
| RE41,376 E | 6/2010 | Torch |
| 7,733,224 B2 | 6/2010 | Tran |
| 7,738,952 B2 | 6/2010 | Yun et al. |
| 7,738,958 B2 | 6/2010 | Zdeblick et al. |
| 7,747,301 B2 | 6/2010 | Cheng et al. |
| 7,747,318 B2 | 6/2010 | John et al. |
| 7,769,442 B2 | 8/2010 | Shafer |
| 7,769,464 B2 | 8/2010 | Gerber et al. |
| 7,775,993 B2 | 8/2010 | Heruth et al. |
| 7,783,362 B2 | 8/2010 | Whitehurst et al. |
| 7,787,946 B2 | 8/2010 | Stahmann et al. |
| 7,790,945 B1 | 9/2010 | Watson, Jr. |
| 7,792,583 B2 | 9/2010 | Miesel et al. |
| 7,801,603 B2 | 9/2010 | Westlund et al. |
| 7,801,618 B2 | 9/2010 | Pless |
| 7,801,743 B2 | 9/2010 | Graves et al. |
| 7,809,442 B2 | 10/2010 | Bolea et al. |
| 7,813,802 B2 | 10/2010 | Tcheng et al. |
| 7,813,812 B2 | 10/2010 | Kieval et al. |
| 7,822,481 B2 | 10/2010 | Gerber et al. |
| 7,827,011 B2 | 11/2010 | DeVaul et al. |
| 7,831,305 B2 | 11/2010 | Gliner |
| 7,847,628 B2 | 12/2010 | Denison |
| 7,848,817 B2 | 12/2010 | Janzig et al. |
| 7,860,570 B2 | 12/2010 | Whitehurst et al. |
| 7,862,826 B2 | 1/2011 | Murphy et al. |
| 7,863,188 B2 | 1/2011 | Tsurume et al. |
| 7,865,244 B2 | 1/2011 | Giftakis et al. |
| 7,866,212 B2 | 1/2011 | Ariav et al. |
| 7,875,611 B2 | 1/2011 | Bain et al. |
| 7,881,780 B2 | 2/2011 | Flaherty |
| 7,884,727 B2 | 2/2011 | Tran |
| 7,899,527 B2 | 3/2011 | Yun et al. |
| 7,899,539 B2 | 3/2011 | Whitehurst et al. |
| 7,899,545 B2 | 3/2011 | John |
| 7,904,158 B2 | 3/2011 | Stegemann et al. |
| 7,925,348 B1 | 4/2011 | Bornzin et al. |
| 7,931,592 B2 | 4/2011 | Currie et al. |
| 7,935,076 B2 | 5/2011 | Estes et al. |

(56) References Cited

U.S. PATENT DOCUMENTS

| | | |
|---|---|---|
| 7,945,316 B2 | 5/2011 | Giftakis et al. |
| 7,953,485 B2 | 5/2011 | Salo et al. |
| RE42,471 E | 6/2011 | Torch |
| 7,957,809 B2 | 6/2011 | Bourget et al. |
| 7,957,820 B2 | 6/2011 | Bertolero et al. |
| 7,959,567 B2 | 6/2011 | Stivoric et al. |
| 7,965,833 B2 | 6/2011 | Meir et al. |
| 7,974,671 B2 | 7/2011 | Fujiwara et al. |
| 7,985,185 B2 | 7/2011 | De Voir et al. |
| 7,991,460 B2 | 8/2011 | Fischell et al. |
| 7,991,461 B2 | 8/2011 | Flaherty et al. |
| 7,996,076 B2 | 8/2011 | Burns et al. |
| 7,999,857 B2 | 8/2011 | Bunn et al. |
| 8,000,789 B2 | 8/2011 | Denison |
| 8,000,794 B2 | 8/2011 | Lozano |
| 8,002,701 B2 | 8/2011 | John et al. |
| 8,008,283 B2 | 8/2011 | Hochman et al. |
| 8,010,194 B2 | 8/2011 | Muller |
| 8,021,299 B2 | 9/2011 | Miesel et al. |
| 8,027,730 B2 | 9/2011 | John |
| 8,027,737 B2 | 9/2011 | Kokones et al. |
| 8,032,213 B1 | 10/2011 | Qu et al. |
| 8,041,418 B2 | 10/2011 | Giftakis et al. |
| 8,041,419 B2 | 10/2011 | Giftakis et al. |
| 8,060,194 B2 | 11/2011 | Flaherty |
| 8,060,206 B2 | 11/2011 | Kieval et al. |
| 8,060,219 B2 | 11/2011 | Ross et al. |
| 8,066,650 B2 | 11/2011 | Lee et al. |
| 8,068,911 B2 | 11/2011 | Giftakis et al. |
| 8,070,695 B2 | 12/2011 | Gupta et al. |
| 8,075,499 B2 | 12/2011 | Nathan et al. |
| 8,079,968 B2 | 12/2011 | Hoffmann |
| 8,084,663 B2 | 12/2011 | Watson, Jr. |
| 8,103,333 B2 | 1/2012 | Tran |
| 8,103,351 B2 | 1/2012 | Gerber et al. |
| 8,108,036 B2 | 1/2012 | Tran |
| 8,108,038 B2 | 1/2012 | Giftakis et al. |
| 8,108,046 B2 | 1/2012 | Giftakis et al. |
| 8,109,891 B2 | 2/2012 | Kramer et al. |
| 8,112,148 B2 | 2/2012 | Giftakis et al. |
| 8,112,153 B2 | 2/2012 | Giftakis et al. |
| 8,114,021 B2 | 2/2012 | Robertson et al. |
| 8,121,673 B2 | 2/2012 | Tran |
| 8,121,690 B2 | 2/2012 | Yun et al. |
| 8,121,694 B2 | 2/2012 | Molnar et al. |
| 8,140,143 B2 | 3/2012 | Picard et al. |
| 8,157,731 B2 | 4/2012 | Teller et al. |
| 8,172,459 B2 | 5/2012 | Abreu |
| 8,172,777 B2 | 5/2012 | Goto |
| 8,180,440 B2 | 5/2012 | McCombie et al. |
| 8,200,320 B2 | 6/2012 | Kovacs |
| 8,200,321 B2 | 6/2012 | McCombie et al. |
| 8,209,009 B2 | 6/2012 | Giftakis et al. |
| 8,209,019 B2 | 6/2012 | Giftakis et al. |
| 8,214,007 B2 | 7/2012 | Baker et al. |
| 8,214,035 B2 | 7/2012 | Giftakis et al. |
| 8,229,535 B2 | 7/2012 | Mensinger et al. |
| 8,239,010 B2 | 8/2012 | Banet et al. |
| 8,249,731 B2 | 8/2012 | Tran et al. |
| 8,265,907 B2 | 9/2012 | Nanikashvili et al. |
| 8,290,574 B2 | 10/2012 | Feild et al. |
| 8,290,577 B2 | 10/2012 | Brooks et al. |
| 8,290,596 B2 | 10/2012 | Wei et al. |
| 8,301,575 B2 | 10/2012 | Bonnet et al. |
| 8,311,620 B2 | 11/2012 | Qu et al. |
| 8,311,645 B2 | 11/2012 | Bolea et al. |
| 8,317,776 B2 | 11/2012 | Ferren et al. |
| 8,321,004 B2 | 11/2012 | Moon et al. |
| 8,323,188 B2 | 12/2012 | Tran |
| 8,323,189 B2 | 12/2012 | Tran et al. |
| 8,326,419 B2 | 12/2012 | Rosenberg et al. |
| 8,328,420 B2 | 12/2012 | Abreu |
| 8,328,718 B2 | 12/2012 | Tran |
| 8,333,874 B2 | 12/2012 | Currie |
| 8,352,034 B2 | 1/2013 | Berg et al. |
| 8,364,250 B2 | 1/2013 | Moon et al. |
| 8,369,936 B2 | 2/2013 | Farringdon et al. |
| 8,386,032 B2 | 2/2013 | Bachinski et al. |
| 8,396,537 B2 | 3/2013 | Balji et al. |
| 8,398,546 B2 | 3/2013 | Pacione et al. |
| 8,398,560 B2 | 3/2013 | Elser |
| 8,401,646 B2 | 3/2013 | Stadler et al. |
| 8,403,881 B2 | 3/2013 | Ferren et al. |
| 8,406,868 B2 | 3/2013 | Buschman et al. |
| 8,410,078 B2 | 4/2013 | Liang et al. |
| 8,417,343 B2 | 4/2013 | Bolea et al. |
| 8,419,649 B2 | 4/2013 | Banet et al. |
| 8,423,134 B2 | 4/2013 | Buschman et al. |
| 8,425,415 B2 | 4/2013 | Tran |
| 8,428,720 B2 | 4/2013 | Corbucci et al. |
| 8,428,727 B2 | 4/2013 | Bolea et al. |
| 8,435,738 B2 | 5/2013 | Holmes |
| 8,437,824 B2 | 5/2013 | Moon et al. |
| 8,443,634 B2 | 5/2013 | Scheffler et al. |
| 8,447,401 B2 | 5/2013 | Miesel et al. |
| 8,449,471 B2 | 5/2013 | Tran |
| 8,452,409 B2 | 5/2013 | Bachinski et al. |
| 2001/0032059 A1 | 10/2001 | Kelly, Jr. et al. |
| 2002/0177882 A1 | 11/2002 | DiLorenzo |
| 2003/0236474 A1 | 12/2003 | Singh |
| 2004/0111045 A1 | 6/2004 | Sullivan et al. |
| 2006/0212097 A1 | 9/2006 | Varadan et al. |
| 2006/0290516 A1 | 12/2006 | Muehlsteff et al. |
| 2007/0249470 A1 | 10/2007 | Niva et al. |
| 2007/0276200 A1 | 11/2007 | Ahola et al. |
| 2007/0287928 A1 | 12/2007 | Kiviniemi et al. |
| 2008/0081958 A1 | 4/2008 | Denison et al. |
| 2008/0134862 A1 | 6/2008 | Lumme et al. |
| 2008/0150731 A1 | 6/2008 | Laukkanen et al. |
| 2008/0214359 A1 | 9/2008 | Niva et al. |
| 2008/0281376 A1 | 11/2008 | Gerber et al. |
| 2008/0319281 A1 | 12/2008 | Aarts |
| 2009/0030345 A1 | 1/2009 | Bonnet et al. |
| 2009/0060287 A1 | 3/2009 | Hyde et al. |
| 2009/0099627 A1 | 4/2009 | Molnar et al. |
| 2009/0105785 A1 | 4/2009 | Wei et al. |
| 2009/0115618 A1 | 5/2009 | Tuulari |
| 2009/0137921 A1 | 5/2009 | Kramer et al. |
| 2009/0156944 A1 | 6/2009 | Kinnunen et al. |
| 2009/0216143 A1 | 8/2009 | Tulppo et al. |
| 2010/0049006 A1 | 2/2010 | Magar et al. |
| 2010/0121214 A1 | 5/2010 | Giftakis et al. |
| 2010/0137735 A1 | 6/2010 | Hoppe |
| 2010/0228103 A1 | 9/2010 | Schecter |
| 2010/0268056 A1 | 10/2010 | Picard et al. |
| 2010/0280574 A1* | 11/2010 | Carlson et al. .................. 607/59 |
| 2010/0298661 A1 | 11/2010 | McCombie et al. |
| 2010/0305665 A1 | 12/2010 | Miesel et al. |
| 2010/0312188 A1 | 12/2010 | Robertson et al. |
| 2011/0060252 A1 | 3/2011 | Simonsen et al. |
| 2011/0066081 A1 | 3/2011 | Goto |
| 2011/0230730 A1 | 9/2011 | Quigg et al. |

OTHER PUBLICATIONS

Zio Card, "Event cardiac activity recording device", iRhythm, San Francisco, CA, Mar. 2009, 2 pages.

* cited by examiner

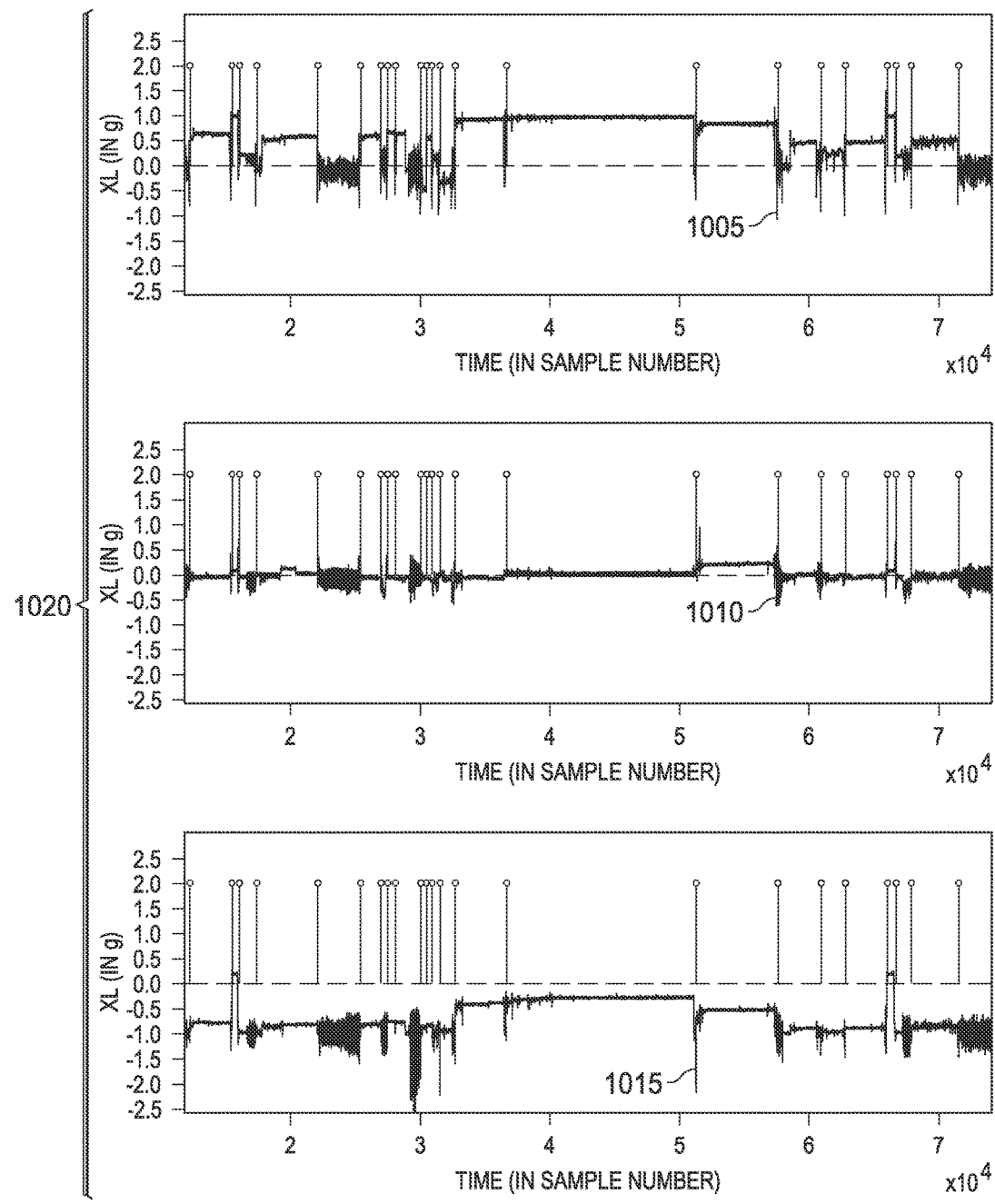

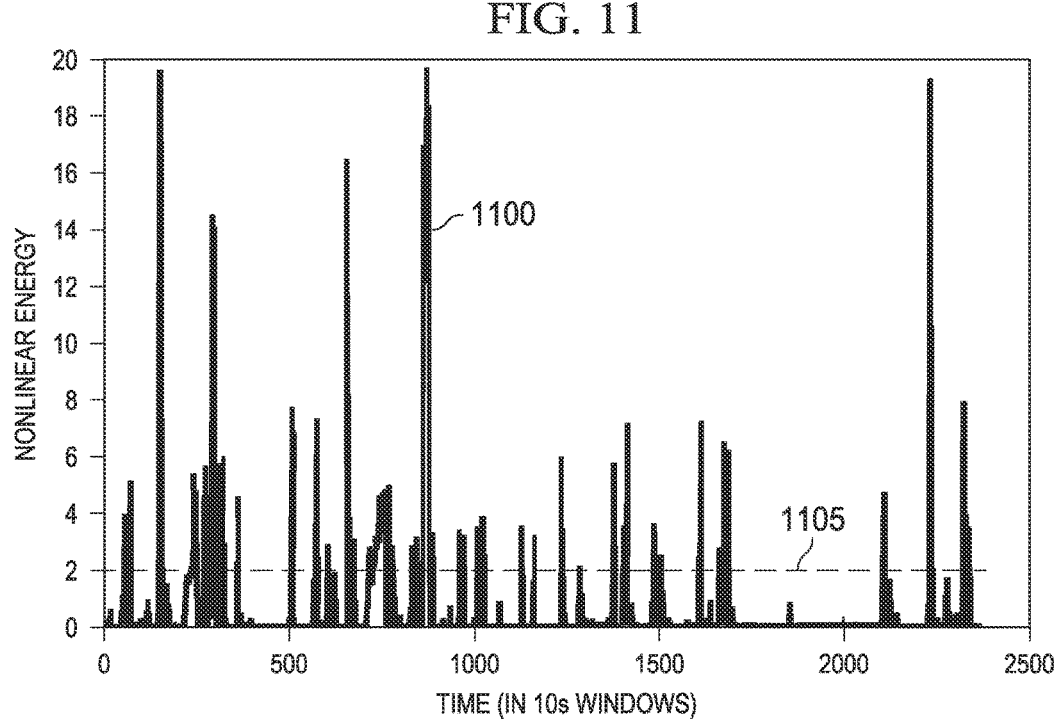

METHODS, SYSTEMS AND APPARATUSES FOR DETECTING SEIZURE AND NON-SEIZURE STATES

CROSS-REFERENCE TO RELATED APPLICATION

This application is related to the following commonly-assigned application entitled "Methods, Systems and Apparatuses for Detecting Increased Risk of Sudden Death," U.S. application Ser. No. 13/453,746, filed May 10, 2012, herein incorporated in its entirety by reference.

BACKGROUND OF THE DISCLOSURE

The present disclosure relates generally to the field of medical systems for detecting seizures. More particularly, the disclosure relates to systems, methods and apparatuses for using an accelerometer based system for detecting seizure and non-seizure states in patients experiencing seizures.

The embodiments described herein relate generally to the field of medical systems for detecting seizures. "A seizure is an abnormal, unregulated electrical charge that occurs within the brain's cortical gray matter and transiently interrupts normal brain function." The Merck Manual of Diagnosis and Therapy, 1822 (M. Beers Editor in Chief, 18th ed. 2006) ("Merck Manual"). Epilepsy is a chronic disease characterized by such seizures, but not caused by an event such as a stroke, drug use, or physical injury. Seizures may vary in frequency and scope and may range from involving no impairment of consciousness at all to complete loss of consciousness. Typically, a seizure resolves within a few minutes and extraordinary medical intervention, other than that needed for the comfort of the patient and to promote unobstructed breathing, is not needed. (See, generally, Merck Manual at 1822-1827, incorporated herein by reference.)

If a patient is aware that a seizure is beginning, the patient may prepare for the seizure by ceasing activity that may be dangerous should a seizure begin, assuming a comfortable position, and/or alerting friends or family. In some patients, an implanted neurostimulator, such as that described in U.S. Pat. No. 5,304,206, incorporated herein by reference, may be activated, which may allow the patient to avoid the seizure, limit the seizure severity and/or duration, or shorten the patient's recovery time. Some patients may not experience onset symptoms indicating that a seizure is imminent or beginning In addition, others may not be aware a seizure has taken place. A record of the frequency, duration, and severity of seizures is an important tool in diagnosing the type of seizures that are occurring and in treating the patient.

Accelerometers have been known for detecting movement in seizure patients. See, for example, U.S. Pat. No. 5,304,206, column 8, lines 28-33. ("A motion sensor is provided within the bracelet for automatically detecting movements by the patient. The motion sensor portion of the detection system 78 (FIG. 6) may be of any known type, such as an accelerometer or a vibration sensor, but preferably, is a contact-type sensor as shown in principal part in FIG. 9.") An accelerometer measures "proper acceleration" of an object. Proper acceleration is different than the more familiar concept of "coordinate acceleration." Coordinate acceleration is a change in velocity of an object with respect to its surroundings, such as an automobile accelerating from zero to 60 miles per hour in a given number of seconds.

By contrast, proper acceleration is the physical acceleration of an object relative to an observer who is in free fall. Proper acceleration is measured in units of "g-force" or gravity/seconds2. Proper acceleration can also be considered to be weight of an object per unit of mass. When an object sits motionless on the ground, its coordinate acceleration is zero. But to determine the object's proper acceleration, one compares the object to the observer in free fall, who is falling towards the center of the Earth. A force acts on the motionless object that is not acting on the observer in free fall: the force of the Earth is pushing up on the object, holding it in place, so the motionless object has a proper acceleration of 1 gravity/second2.

An accelerometer may be used to determine a sudden change of position of a person, which might be indicative of a seizure in the person with physical symptoms. Both the amplitude of the change in position and the frequency of the change in position could be important indications of a seizure, depending in part on how seizures affect a particular patient. Of course, a change of position may have a non-seizure cause, as people sometimes engage in strenuous activities. Most algorithms used to analyze accelerometer data are highly complex, making them inconvenient to use. The use of some accelerometer algorithms requires training and position correction. Most of the current algorithms used to analyze accelerometer data also require that the accelerometer be held in a proper orientation.

Accordingly, a need is present for methods, systems and apparatuses to better detect seizures and/or overcome issues discussed above.

SUMMARY

The embodiments of the disclosure described herein include a system including at least one accelerometer positioned on a patient and configured to collect acceleration data and a processor in communication with the at least one accelerometer and configured to receive acceleration data from the at least one accelerometer. The processor may apply one or more non-linear operators to the acceleration data to determine whether the acceleration data indicates an event. Application of the non-linear operator to the acceleration data may include calculation of a non-linear energy of the acceleration data and performance of at least one secondary analysis to determine whether the event is a seizure.

The embodiments of the present disclosure also include an apparatus, which includes at least one accelerometer for positioning on a patient, the at least one accelerometer configured to collect acceleration data and a processor in communication with the at least one accelerometer, configured to receive acceleration data from the at least one accelerometer. The processor is configured to apply a non-linear operator to the acceleration data to determine whether the acceleration data indicates an event, wherein application of the non-linear operator to the acceleration data includes calculation of a non-linear energy of the acceleration data and performance of at least one secondary analysis to determine whether the event is a seizure.

The embodiments of the present disclosure also include a method. The steps of the method include receiving acceleration data at a processor from at least one accelerometer positioned on the patient and applying a non-linear operator to the acceleration data at the processor to determine whether the acceleration data indicates an event, wherein applying the non-linear operator to the acceleration data includes calculating a non-linear energy of the acceleration data.

Other aspects and advantages of the embodiments described herein will become apparent from the following description and the accompanying drawings, illustrating the principles of the embodiments by way of example only.

BRIEF DESCRIPTION OF THE DRAWINGS

Features and advantages of the present disclosure will become apparent from the appended claims, the following detailed description of one or more example embodiments, and the corresponding figures.

FIGS. 10A-B depict an example of three channels of accelerometer data as sent from the accelerometer to the processor, in accordance with one or more embodiments of the present disclosure. FIG. 10B is an expanded version of a portion of FIG. 10A.

FIG. 11 depicts the average non-linear energy $\Psi$ of the same three channels of accelerometer data, in accordance with one or more embodiments of the present disclosure.

Figure 1A:
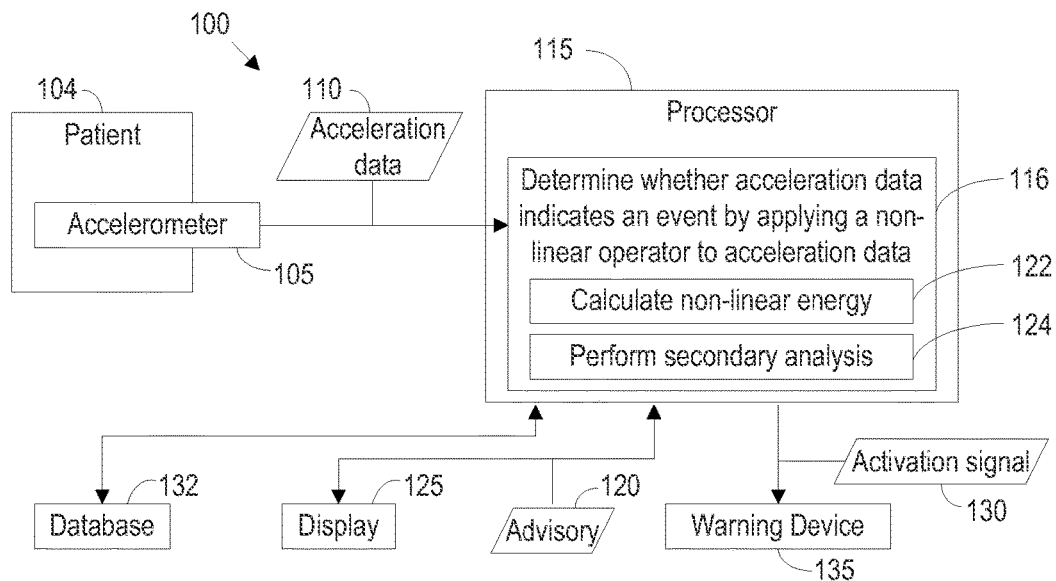
FIGS. 1A-D include schematics and flow diagrams corresponding to a seizure detection device, in accordance with one or more embodiments of the present disclosure.

While the disclosure is subject to various modifications and alternative forms, specific embodiments thereof are shown by way of example in the drawings and the accompanying detailed description. It should be understood, however, that the drawings and detailed description are not intended to limit the disclosure to the particular embodiments. This disclosure is instead intended to cover all modifications, equivalents, and alternatives falling within the scope of the present disclosure as defined by the appended claims.

DETAILED DESCRIPTION

The drawing figures are not necessarily to scale and certain features may be shown exaggerated in scale or in somewhat generalized or schematic form in the interest of clarity and conciseness. In the description which follows, like parts may be marked throughout the specification and drawing with the same reference numerals. The foregoing description of the figures is provided for a more complete understanding of the drawings. It should be understood, however, that the embodiments are not limited to the precise arrangements and configurations shown. Although the design and use of various embodiments are discussed in detail below, it should be appreciated that the present disclosure provides many inventive concepts that may be embodied in a wide variety of contexts. The specific aspects and embodiments discussed herein are merely illustrative of ways to make and use the disclosure, and do not limit the scope of the disclosure. It would be impossible or impractical to include all of the possible embodiments and contexts of the disclosure in this disclosure. Upon reading this disclosure, many alternative embodiments of the present disclosure will be apparent to persons of ordinary skill in the art.

FIG. 1A depicts a schematic of a seizure detection device 100 in accordance with an embodiment of the present disclosure. The seizure detection device 100 comprises an accelerometer 105 on a patient 104, a processor 115, a display 125 and a warning device 135. The accelerometer 105 sends accelerometer data (also called "acceleration data" or "XL data" herein) 110 to the processor 115 running appropriate software. The processor 115 may be configured to determine, at 116, whether the acceleration data 110 indicates an event is a seizure event or a non-seizure event by application of at least one non-linear operator to the acceleration data 110. Application of the non-linear operator to the acceleration data 110 by the processor 115 may include a calculation, at 122, of the non-linear energy of the acceleration data and performance, at 124, of at least one secondary analysis to determine whether the event is a seizure. An advisory 120 can be sent to the display 125 as to whether the event is a seizure event or not a seizure event. In addition, the same non-linear operator may be applied successively to the acceleration data 110, or one or more other non-linear operators may be applied in addition to the non-linear operator.

If the event is a seizure event, the processor 115 can also send an activation signal 130 to the warning device 135. The warning device 135 could, for example, activate an alarm with a sound or a vibration. The warning device 135 could also place a call with a recorded message, or send an e-mail or a text message, to one or more designated persons. In addition, a therapy, such as electrical stimulation to a cranial nerve or brain tissue, may be provided in place of, simultaneously with, or following the warning provided by the warning device 135.

Continuing to refer to FIG. 1A, the processor 115 could retain a record, for example, of all events, their onset, timing, and/or duration and noting the XL data or other measurements made at the time of the event and whether the event was determined to be a seizure. Alternatively, the record might only include events that were determined to be seizures. The record could be stored on a database 132 in communication with the processor 115 and data from the record, for example, taken over particular time periods could be sent to the display 125 (or to secondary displays) for graphical or text display, either on demand or on a periodic basis. The record could also be downloaded onto one or more additional processors for convenience or further analysis. The record could also be sent wirelessly, or otherwise, to a remote server or to a cloud computing interface for further processing.

Figure 1B:
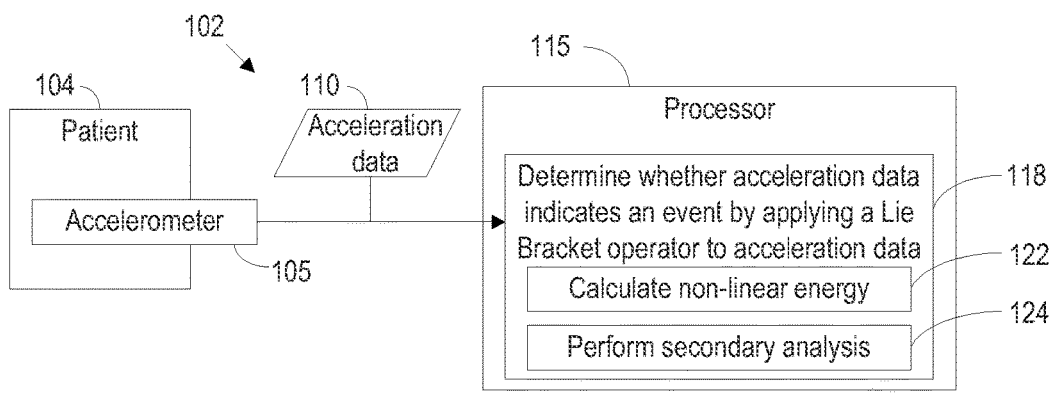

FIG. 1B depicts a schematic of a seizure detection device 102 in accordance with an embodiment of the present disclosure. The seizure detection device 102 comprises an accelerometer 105 on a patient 104, and a processor 115. The accelerometer 105 sends acceleration data 110 to the processor 115 running The processor 115 determines, at 118, whether the acceleration data 110 indicates an event is a seizure event or a non-seizure event by applying a Lie Bracket operator to the acceleration data 110. Application of the Lie Bracket operator to the acceleration data 110 by the processor 115 may include a calculation, at 122, of the non-linear energy of the acceleration data and performance, at 124, of at least one secondary analysis to determine whether the event is a seizure.

Continuing to refer to FIGS. 1A-B, the seizure detection devices 100 and 102 might include the accelerometer 105, the processor 115, the display 125, the warning device 135, and the database 132 in a single housing. Alternatively, one or more elements of the seizure detection device could be housed separately, and exchange communications, either through wires or wirelessly.

In one of more alternative embodiments of the present disclosure, other position detection devices may be used in place of, or in addition to an accelerometer, and the analysis provided as part of those embodiments of the disclosure could be adjusted, if necessary to accommodate any differences needed to use the alternative position detection devices. A gyroscope is another example of a device which can determine a change in a position of a person. While an accelerometer may give greater sensitivity to linear changes in position, a gyroscope may have greater sensitivity for angular motion, and may be considered an appropriate component for use with specific types of seizures or for specific patients who may experience seizures in which angular motion is an important component. Other position detection devices could also be used as part of the present disclosure.

Figure 1C:
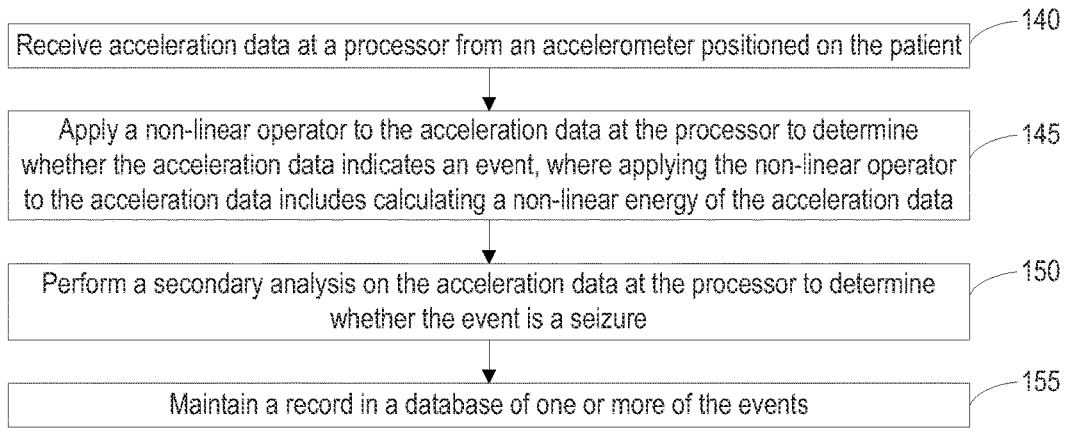

FIG. 1C is a flow diagram corresponding to a method of using a seizure detection device in accordance with one or more embodiments of the present disclosure. The processor receives acceleration data from an accelerometer positioned on the patient at 140. At 145, the processor applies a non-linear operator to the acceleration data to determine whether the acceleration data indicates an event. Applying the non-linear operator to the acceleration data includes calculating a non-linear energy of the acceleration data. At 150, the processor performs a secondary analysis on the acceleration data to determine whether the event is a seizure event. At 155, a record of the one or more events is maintained in a database.

Figure 1D:
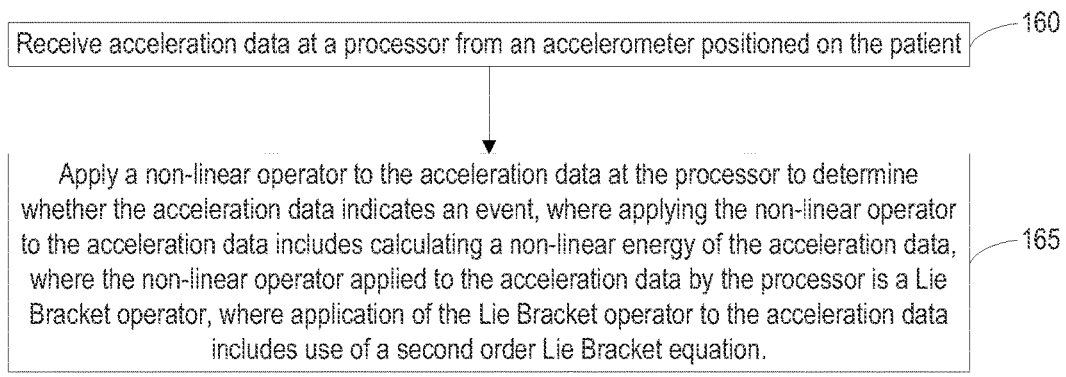

FIG. 1D is a flow diagram corresponding to a method of using a seizure detection device in accordance with one or more embodiments of the present disclosure. The processor receives acceleration data from an accelerometer positioned on the patient at 160. At 165, the processor applies a non-linear operator to the acceleration data to determine whether the acceleration data indicates an event. Applying the non-linear operator to the acceleration data includes calculating a non-linear energy of the acceleration data. The non-linear operator may be a Lie Bracket operator and application of the Lie Bracket operator to the acceleration data may include use of a second order Lie Bracket equation.

Figure 2A:
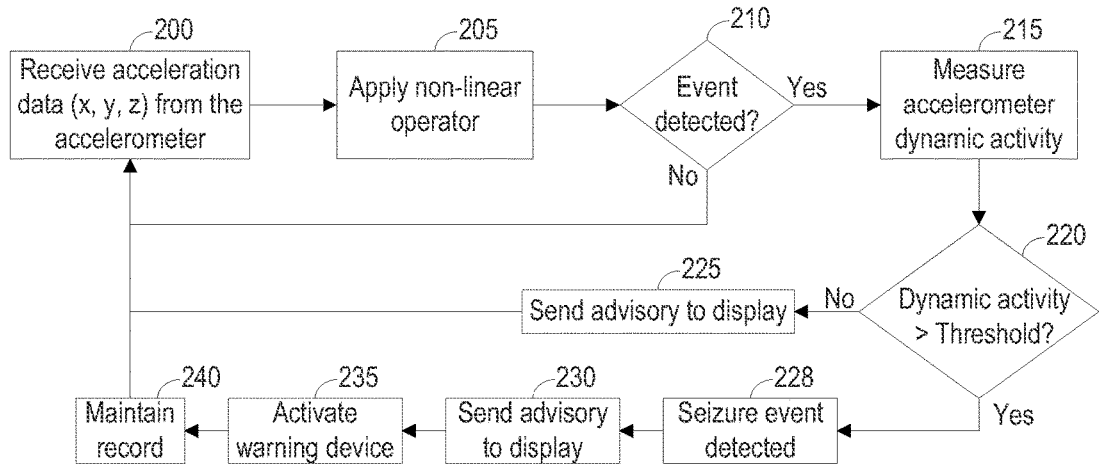
FIGS. 2A-B include flow diagrams of a seizure detection process in accordance with one or more embodiments of the present disclosure, using accelerometer data and considering dynamic activity.

FIG. 2A is a flowchart of a seizure detection process in accordance with one or more embodiments of the present disclosure, using accelerometer data and considering dynamic activity. The process depicted in FIG. 2A could be used for example, with the seizure detection device 100 depicted in FIG. 1A. Accelerometer data collected from an accelerometer on the patient's person is received 200 at the processor. The processor may be configured to apply 205 non-linear operators (also called non-linear estimators herein) to the acceleration data, which is used to determine whether an event has been detected 210. If an event has not been detected according to the accelerometer data, the process of receiving the accelerometer data at the processor for analysis continues. If an event has been detected, accelerometer dynamic activity is measured and analyzed 215. The accelerometer dynamic activity is compared 220 to a first predetermined threshold.

The first predetermined threshold may be determined empirically. The predetermined threshold may be set in a factory to a specific value or may be set (or adjusted) by a physician supervising the condition of a patient. The predetermined threshold might vary for different patients, who might experience widely varying degrees of movement during seizure, or for different types of seizure conditions. One or more embodiments of the present disclosure may include a learning function for determining the first predetermined threshold. For example, a patient who is very athletic or who is engaged in certain vigorous activities, such as dance, gymnastics or martial arts, may make abrupt movements during ordinary activity. If the device renders false positives because the predetermined threshold is set too low, a feedback mechanism may be used to help the device "learn" to screen out false positives. This learning process may be provided acutely in a real-time fashion, chronically over a long period using neural networks and pattern recognition based approaches, or a combination thereof.

If the dynamic activity is not greater than the predetermined first threshold, an advisory that there has been a "Non-Seizure" event may be sent 225 to the display, while accelerometer data continues to be received at the processor. If the accelerometer dynamic activity is greater than the predetermined first threshold, a seizure event is detected 228 and a "Seizure Event" advisory may be sent 230 to the display and the warning device may be activated 235. When activated 235, the warning device could, for example, activate an alarm with a sound or a vibration. The warning device could also place a call with a recorded message, or send a message, such as an e-mail or a text message, to one or more designated persons.

In some patients, a seizure may manifest as a cessation of movement; that is, the patient may be motionless and/or appear to be in a coma. In such a case or for such conditions, in accordance with one of more embodiments of the present disclosure, if the accelerometer dynamic activity is less than a predetermined first threshold having a low value, a "Seizure Event" advisory may be sent 230 to the display and the warning device may be activated 235. In one or more embodiments of the present disclosure, there could be a first high pre-determined threshold and a first low predetermined threshold, with a "Seizure Event" advisory being sent 230 to the display and the warning device being activated 235 both if the accelerometer dynamic activity is less than the first low predetermined threshold or if the accelerometer dynamic activity is more than the first high predetermined threshold.

Continuing to refer to FIG. 2A, the processor could maintain 240 a record of seizure events (or, alternatively, both seizure and non-seizure events), their onset, timing and/or duration, and noting the XL data or other measurements made at the time of the event. The record could be stored on a database (not separately depicted in FIG. 2) in communication with the processor. Data from the record collected over particular time periods could be sent to the display (or to secondary displays) for graphical or text display, either on demand or on a periodic basis. The record could also be downloaded onto one or more additional processors for convenience or further analysis. The returns to the input of the accelerometer data indicate that measurements preferably continue regardless of the findings of whether there is a seizure (unless, for example, the accelerometer is intentionally turned off).

Figure 2B:
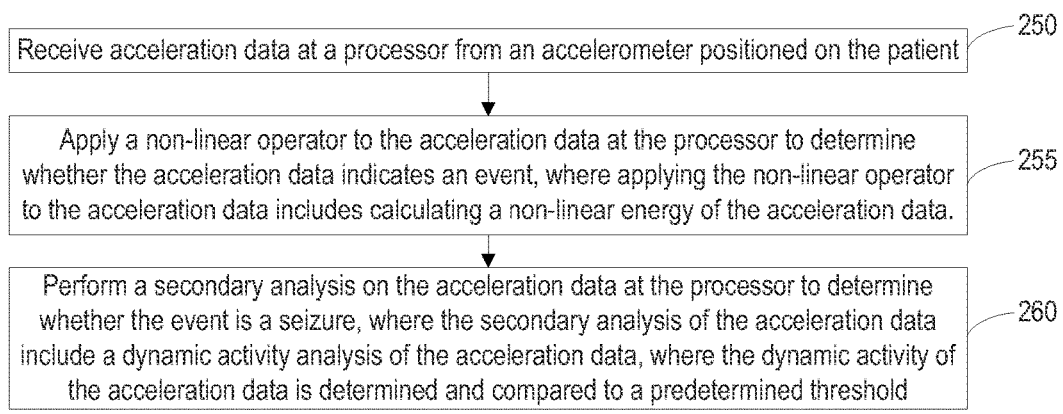

FIG. 2B is a flow diagram corresponding to a method of using a seizure detection device in accordance with one or more embodiments of the present disclosure. The processor receives acceleration data from an accelerometer positioned on the patient at 250. At 255, the processor applies a non-linear operator to the acceleration data to determine whether the acceleration data indicates an event. Applying the non-linear operator to the acceleration data includes calculating a non-linear energy of the acceleration data. At 260, the processor performs a secondary analysis on the acceleration data to determine whether the event is a seizure event. The secondary analysis of the acceleration data may include a dynamic activity analysis of the acceleration data, where the dynamic activity of the acceleration data is determined and compared to a predetermined threshold.

Figure 3A:
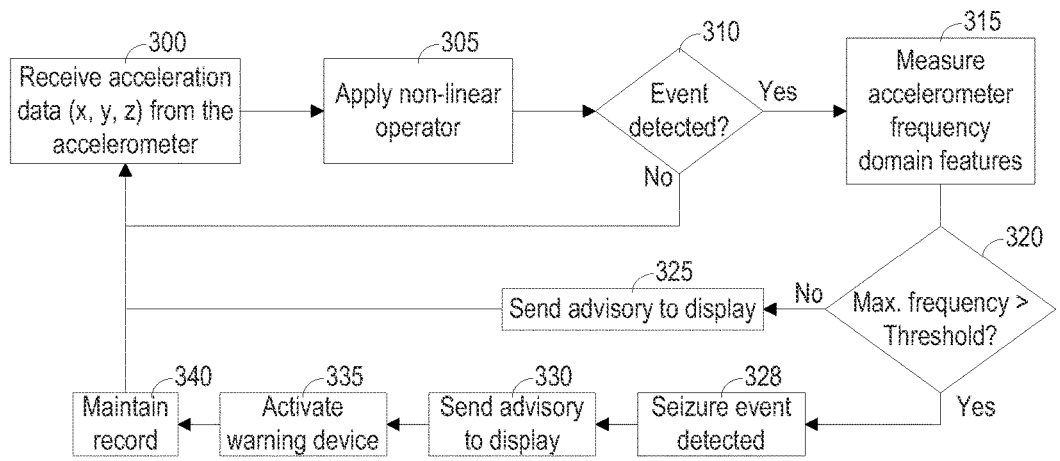
FIGS. 3A-B include flow diagrams of a seizure detection process in accordance with one or more embodiments of the present disclosure, using accelerometer data and considering accelerometer frequency domain features.

FIG. 3A is a flowchart of a seizure detection process in accordance with one or more embodiments of the present disclosure, using accelerometer data and considering accelerometer frequency domain features. The process of FIG. 3A could be used, for example, with the device depicted in FIG. 1. Accelerometer data collected from an accelerometer on the patient's person is received 300 at a processor running appropriate software. The processor applies 305 non-linear operators to the acceleration data to determine whether an event has been detected 310. If an event has not been detected, the process of receiving the acceleration data at the processor for analysis continues. If an event has been detected, frequency domain features of the acceleration data are measured 315 to determine a maximum frequency. The maximum frequency is compared 320 to a second predetermined threshold. If the maximum frequency is not greater than the second predetermined threshold, an advisory that there has been a "Non-Seizure Event" may be sent 325 to the display. Acceleration data continues to be received at the processor. If the maximum frequency is greater than the second predetermined threshold, a seizure event is detected 328 and a "Seizure Event" advisory may be sent 330 to the display and the warning device is activated 332. The warning device when activated could, for example, activate an alarm with a sound or a vibration. The warning device could also place a call with a recorded message, or send a text message, to designated person(s).

Like the first predetermined threshold, the second predetermined threshold may be determined empirically or based on adaptive learning over time. The second predetermined threshold may be set at a factory or may be set (or adjusted) by a treating physician to reflect the situation of a particular patient or condition being treated. As with the first predetermined threshold, the value of the second predetermined threshold may be set low for a seizure manifesting as a cessation of movement, so that if the maximum frequency is less than the predetermined first threshold, a "Seizure Event" advisory is sent 330 to the display and the warning device is activated 335. And in one or more embodiments of the present disclosure, there could be a second high predetermined threshold and a second low predetermined threshold used, with a "Seizure Event" advisory being sent 330 to the display and the warning device being activated 335 both if the maximum frequency is less than the second low predetermined threshold or if the maximum frequency is more than the second high predetermined threshold.

Continuing to refer to FIG. 3A, the processor could maintain 340 a record, for example, of all seizure events, their onset, timing and/or duration and noting the XL data or other measurements made at the time of the event. Alternatively, a record could be maintained by the processor for all events, not just seizure events. The record could be stored on a database within the processor and data from one or more time periods could be sent to the display (or secondary displays) for graphical or text display, either on demand or on a periodic basis. The record could also be downloaded onto one or more additional processors for convenience or further analysis. In additional embodiments, the processor could maintain a patient-specific library with a learning function, so that the present disclosure could be more specifically adjusted to the patient's pattern of seizures.

Referring again to FIG. 3A, returns to the input of the accelerometer data at various points in the flowchart indicate that measurements preferably continue regardless of the findings of whether there is a seizure (unless, for example, the accelerometer is intentionally turned off).

Figure 3B:
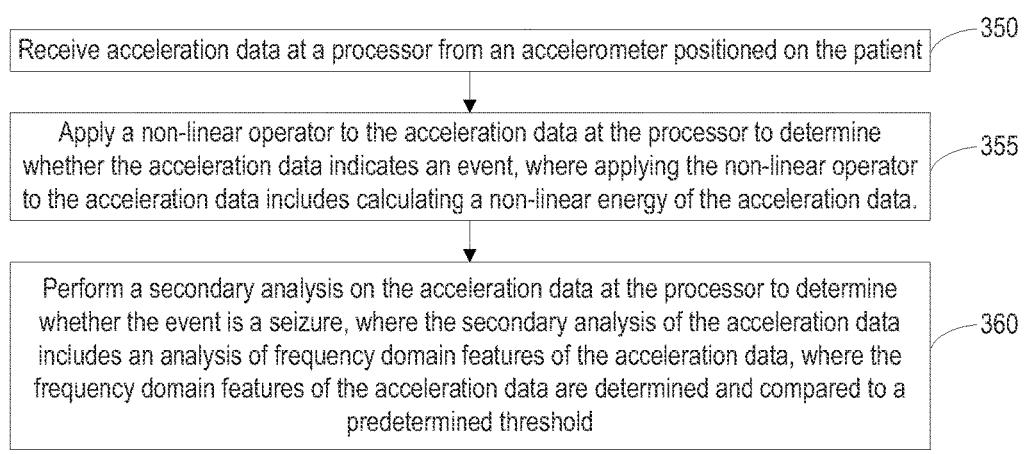

FIG. 3B is a flow diagram corresponding to a method of using a seizure detection device in accordance with one or more embodiments of the present disclosure. The processor receives acceleration data from an accelerometer positioned on the patient at 350. At 355, the processor applies a non-linear operator to the acceleration data to determine whether the acceleration data indicates an event. Applying the non-linear operator to the acceleration data includes calculating a non-linear energy of the acceleration data. At 360, the processor performs a secondary analysis on the acceleration data to determine whether the event is a seizure event. The secondary analysis of the acceleration data may include an analysis of frequency domain features of the acceleration data, where the frequency domain features of the acceleration data are determined and compared to a predetermined threshold.

Figure 4:
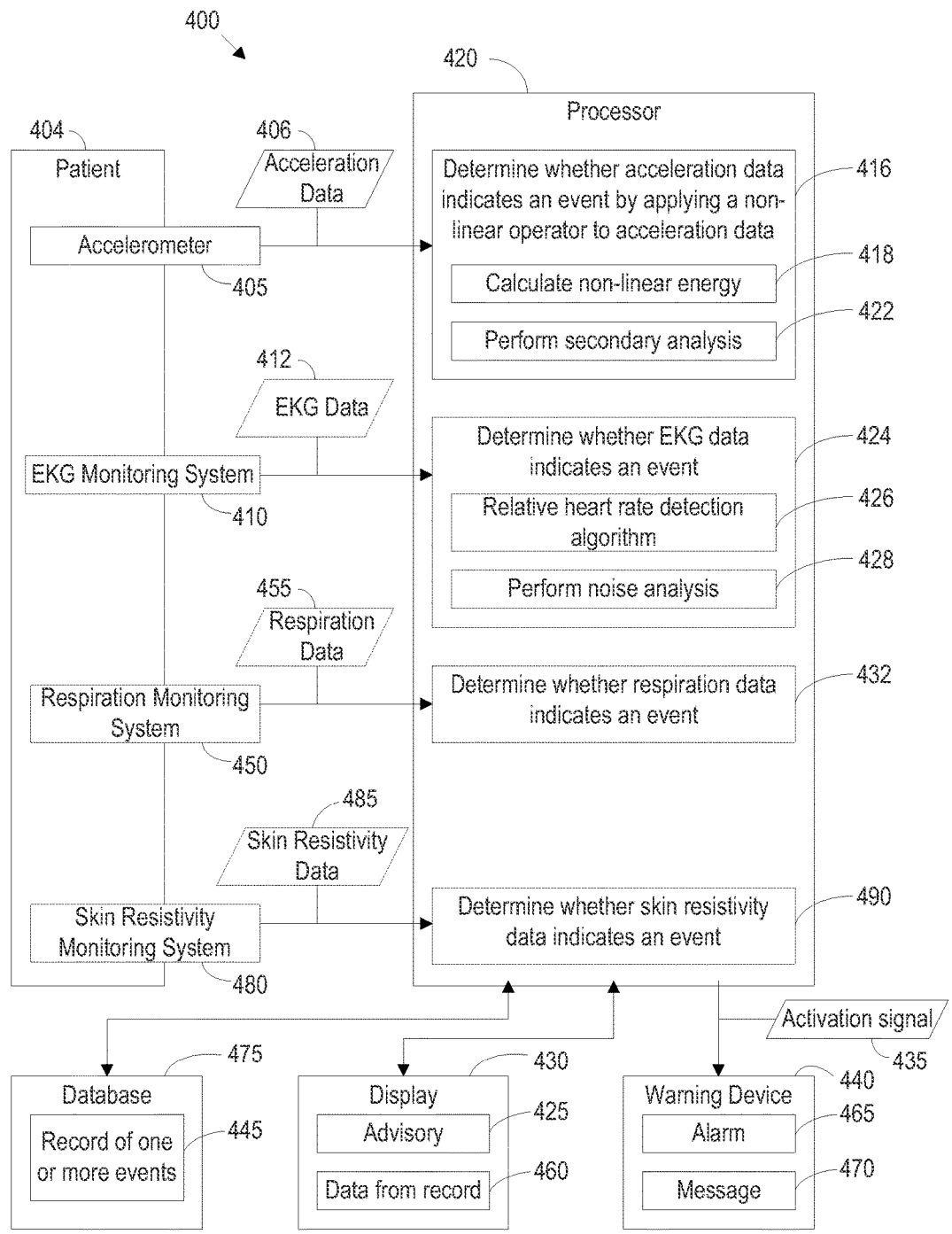
FIG. 4 depicts a schematic of a system of seizure detection in accordance with one or more embodiments of the present disclosure, using physiological monitoring systems, such as EKG monitoring systems and respiration monitoring systems, in addition to accelerometer data.

FIG. 4 depicts a schematic of a seizure detection system 400 in accordance with one or more embodiments of the present disclosure, using one or more physiological monitoring systems in addition to an accelerometer, such as an electrocardiogram ("EKG" or "ECG") monitoring system 410, a respiration monitoring system 450, or a skin resistivity monitoring system 480. The seizure detection system 400 of FIG. 4 may include an accelerometer 405 on a patient 404, an EKG monitoring system 410, a respiration monitoring system 450, a processor 420, a display 430, a warning device 440, and a database 445. The accelerometer 405 may be configured to send accelerometer data 406 to the processor 420. The EKG monitoring system 410 may be configured to send EKG data 412 of the patient's heart activity to the processor 420. The respiration monitoring system 450 may be configured to send respiration data 455 of the patient's respiration activity to the processor 420. The skin resistivity monitoring system 480 may be configured to send skin resistivity data 485 of the patient's skin resistivity activity to the processor 420.

The processor 420 may be configured to determine, at 416, whether the acceleration data 406 indicates an event is a seizure event or a non-seizure event by applying a non-linear operator to the acceleration data 406. Application of the non-linear operator to the acceleration data 406 by the processor 420 may include a calculation, at 418, of the non-linear energy of the acceleration data and performance, at 422, of at least one secondary analysis to determine whether the event is a seizure.

The processor 420 may be further configured to use physiological monitoring systems other than, or in addition to, the accelerometer 405, indicate an event. The physiological monitoring systems may include the EKG monitoring system 410, the respiration monitoring system 450, the skin resistivity monitoring system 480. For example, the processor 420 may be configured to determine, at 424, whether the EKG data 412 or (EKG measurements) indicates an event and/or whether the event is a seizure event. The processor 420 may be configured to use a relative heart rate detection algorithm 426 to support the determination of whether the event was a seizure. The processor 420 may be further configured to use a noise analysis 428 and/or noise filtering of the EKG data 412 (or EKG measurements) to determine whether to disregard the EKG data 412 in determining whether an event is a seizure when the level of noise in the EKG data 412 is too high. The processor 420 may be further configured to determine, at 432, whether the respiration data 455 indicates an event and/or whether the event is a seizure event. The processor 420 may be further configured to determine, at 490, whether the skin resistivity data 485 indicates an event and/or whether the event is a seizure event. A seizure event could be determined if only one of the accelerator data 406, the EKG data 412, and the respiration data 455 supports a seizure event, but in most cases, it is preferable that a seizure event is determined if the accelerator data 406, the EKG data 412, the respiration data 455, and skin resistivity data 485 all support a finding of a seizure event. (This would reduce false positive findings of a seizure.)

If there is an event, a determination is made as to whether it is a seizure event or a non-seizure event and an appropriate advisory 425 may be sent to the display 430. If the event is a seizure event, the processor 420 may be configured to send an activation signal 435 to the warning device 440. The activated warning device 440 could, for example, activate an alarm 465, such as with a sound or a vibration. The warning device 440 could also provide a message 470 to one or more designated persons. For example, the warning device could place a call with a recorded message, or send a message such as an e-mail or a text message.

Continuing to refer to FIG. 4, the processor 420 could maintain a record 445 of one or more events. For example, the record 445 of the one or more events may include all seizure events, their onset, timing and/or duration, noting the acceleration data or other measurements made at the time of the event. Alternatively, a record could be maintained for all events, not just seizure events. The record 445 may be stored at a database 475 in communication with the processor 420. The database 475 may be located on a mass storage device such as a hard disk drive, solid state drive, memory card, USB key or similar device. The data 460 from the record 445 over one or more time periods may be sent to the display 430 (or to other secondary displays) for display, for example, as graphs or text, either on demand or periodically. The record could be transmitted to designated persons such as the patient's doctors or other medical personnel. The record 445 could also be downloaded onto one or more additional processors for convenience or further analysis.

Referring again to FIG. 4, preferably the inputs from one or more of the accelerometer 405, the EKG monitoring system 410, and the respiration monitoring system 450 continue regardless of the findings of whether an event is a seizure until, for example, the accelerometer and/or the one or more physiological monitoring systems are intentionally turned off.

Continuing to refer to FIG. 4, the seizure detection device 400 might include the accelerometer 405, the EKG monitoring system 410, the respiration monitoring system 450, the processor 420, the display 430, the warning device 440, and the database 475, in a single housing. Alternatively, the elements of the seizure detection device could be housed separately, and exchange communications, either through wires or wirelessly.

In one or more embodiments of the present disclosure, when the seizure detection device detects a probable seizure, the seizure detection device could alert a SUDEP risk detection device, such as described in co-pending and commonly assigned application entitled "Methods, Systems and Apparatuses for Detecting Increased Risk of Sudden Death," U.S. application Ser. No. 13/453,746, filed May 10, 2012 concurrently herewith, to activate the SUDEP device to a greater sensitivity. If the SUDEP device is programmed appropriately, the SUDEP detection device could respond to the alert by sending an acknowledgement to the seizure detection device of the instant disclosure. If the seizure device does not receive an acknowledgement, the processor could activate the warning device to issue an additional warning that the SUDEP detection device might not be functioning properly.

In one or more embodiments of the present disclosure, the accelerometer could include a setting to indicate when the patient will be engaged in different levels of activity, such as strenuous activity, normal activity, sedentary activity or sleeping. The activity levels could be linked to different predetermined thresholds, so that the thresholds are higher for more strenuous activity.

Figure 5:
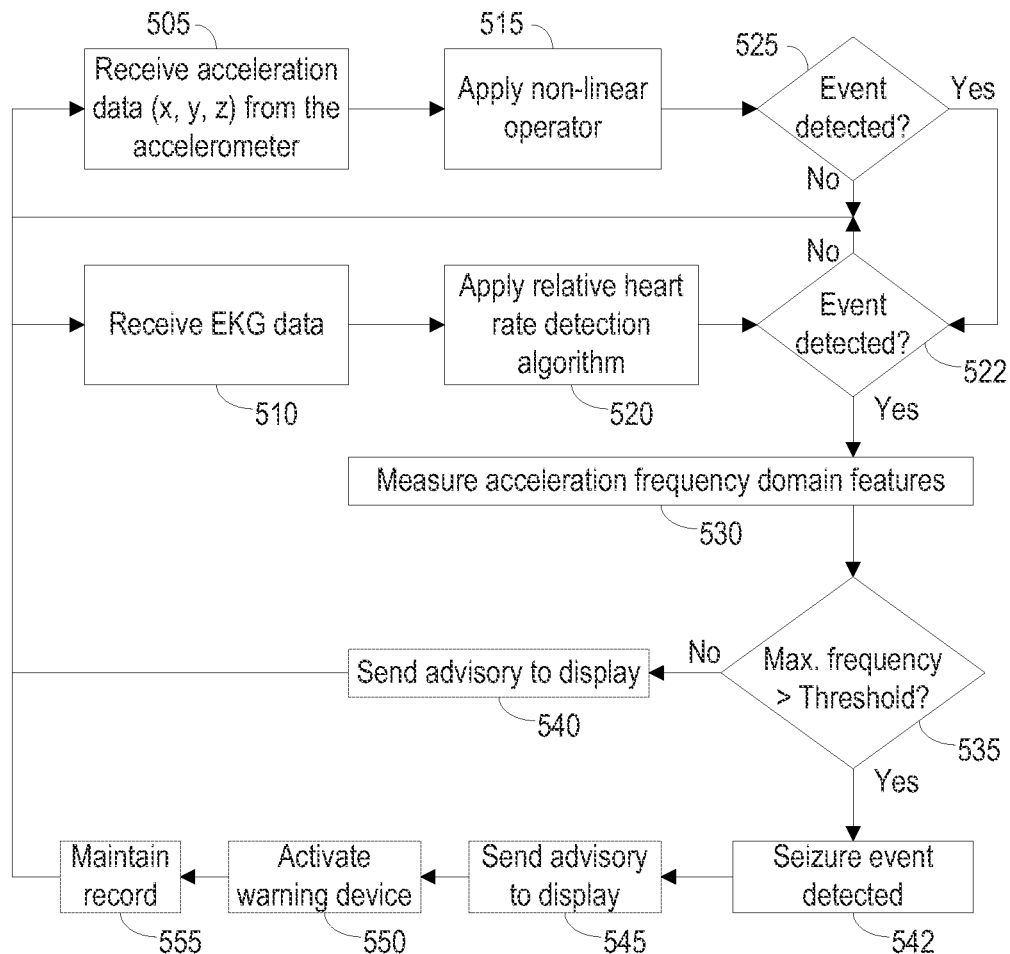
FIG. 5 is a flowchart of a seizure detection process in accordance with one or more embodiments of the present disclosure, using EKG measurements and frequency domain features, in addition to accelerometer data.

FIG. 5 is a flowchart of a seizure detection process in accordance with one or more embodiments of the present disclosure, using EKG data as well as accelerometer data and using measurement of frequency domain features. This process could be used, for example, with the seizure detection system 400 of FIG. 4. Accelerometer data collected from an accelerometer on the patient's person may be received 505 at a processor. EKG data from an EKG monitoring system corresponding to activity of the patient's heart may be received 510 at the processor. The processor may be configured to apply a non-linear operator to the accelerometer data at 515 and determines whether the accelerometer data indicates that an event has occurred at 525. In addition, the processor may be configured to apply a relative heart rate detection algorithm at 520 to the EKG data. After an event has been detected from the accelerometer data, the processor determines at 522 whether an event was also indicated by the EKG data. If either the accelerometer data or the EKG data indicate an event has not been detected, the process of receiving the accelerometer data and the EKG data to the processor for analysis continues. If the EKG data also supports a finding that an event has occurred, then frequency domain features of the accelerometer data are measured 530 to determine a maximum frequency. The maximum frequency is compared 535 to a predetermined threshold. If the maximum frequency is not greater than the predetermined threshold, an advisory that there has been a "Non-Seizure Event" may be sent 540 to the display. Accelerometer data and EKG data continue to be received and continue to be sent to the processor. If the maximum frequency is greater than the predetermined threshold, the processor may be configured to detect a seizure event at 542. The processor may further be configured to send 545 a "Seizure Event" advisory to the display and activate 550 the warning device. The warning device when activated could, for example, activate an alarm with a sound, a flashing light and/or a vibration, as examples. The warning device could also place a call with a recorded message, or send a message such as an e-mail or a text message, to designated person(s).

Continuing to refer to FIG. 5, the processor could maintain 555 a record, for example, of all seizure events, their onset, timing and/or duration, and noting the XL data or other measurements made at the time of the event. Alternatively, a record could be maintained by the processor for all events, not just seizure events. The record over one or more time periods could be sent to the display (or to secondary displays) for graphical or text display, either on demand or periodically. The record could also be downloaded onto one or more additional processors for convenience or further analysis. The record could be maintained on a database accessible to the processor.

Referring again to FIG. 5, returns to the input of the accelerometer data and the input of the EKG data at various points in the flowchart indicate that measurements preferably continue regardless of the findings of whether there is a seizure (unless, for example, the accelerometer or the EKG monitor is intentionally turned off). In alternative embodiments, XL dynamic activity can be measured and compared to a first predetermined threshold, rather than determining the maximum frequency of the frequency domain features and comparing the maximum frequency to the second predetermined threshold, as depicted in FIG. 5.

In some embodiments of the present disclosure, the processor may determine that the EKG measurements contain too much noise and thus determine that the EKG measurements should be ignored. For example, if the application of the non-linear operator indicates substantial movement, it may indicate that there may be noise on the EKG from muscle movement. The processor may ignore the EKG measurements and instead assess whether other measurements, such as accelerometer data, are indicative of a seizure.

In one or more embodiments of the present disclosure, the combination of accelerometer data and EKG data collected may be used to classify the seizure types experienced by a patient. Thus, the patient's condition may be better diagnosed, classified and treated. Table 1 and Table 2 below depict how the collected accelerometer data and EKG data may be used for classification of seizure types:

TABLE 1

Patient population: Generalized Seizures

| | Algorithm Features | | | | | | Algorithm expected performance | |
| | EKG | | | Accelerometer | | | | |
| Seizure Type | Tachycardia | Bradycardia | No change | Shorter-time changes | Longer-time changes | No change | Sensitivity | Specificity |
|---|---|---|---|---|---|---|---|---|
| Tonic-Clonic | X | | | X | X | | X | X |
| Clonic w/out tonic | X | | | X | X | | X | X |
| Clonic with tonic | X | | | | X | | X | X |
| Typical absence | | | X | | | X | | |
| Atypical absence | | | X | X | | | | X |
| Myoclonic absence | X | X | X | X | | | | X |
| Tonic | X | X | | X | | | X | X |
| Myoclonic | | | X | X | | | | X |
| Myoclonic Tonic | X | X | | X | | | X | X |
| Atonic | X | X | | X | | | X | ? |
| Neocortical temporal lobe | | | | | | | | |

TABLE 2

Patient population: Partial Seizures

| | Algorithm Features | | | | | | Algorithm performance requirement | |
| | EKG | | | Accelerometer | | | | |
| Seizure Type | Tachycardia | Bradycardia | No change | Shorter-time changes | Longer-time changes | No change | Sensitivity | Specificity |
|---|---|---|---|---|---|---|---|---|
| Simple Partial | | | | | | | | |
| Partial sensory: Occipital/parietal | | | | X | | X | | |
| Partial sensory: Temporal occipital/parietal | X | | | X | | X | | |
| Partial motor clonic | X | | | X | X | | X | X |
| Partial motor tonic | X | | | X | X | | X | X |

TABLE 2-continued

Patient population: Partial Seizures

| | Algorithm Features | | | | | | Algorithm performance requirement | |
|---|---|---|---|---|---|---|---|---|
| | EKG | | | Accelerometer | | | | |
| Seizure Type | Tachycardia | Bradycardia | No change | Shorter-time changes | Longer-time changes | No change | Sensitivity | Specificity |
| Complex Partial | | | | | | | | |
| Mesial temporal lobe Gelastic | X | | X | X | X | | X | X |
| Secondarily generalized | X | | | X | X | | X | X |

Figure 6:
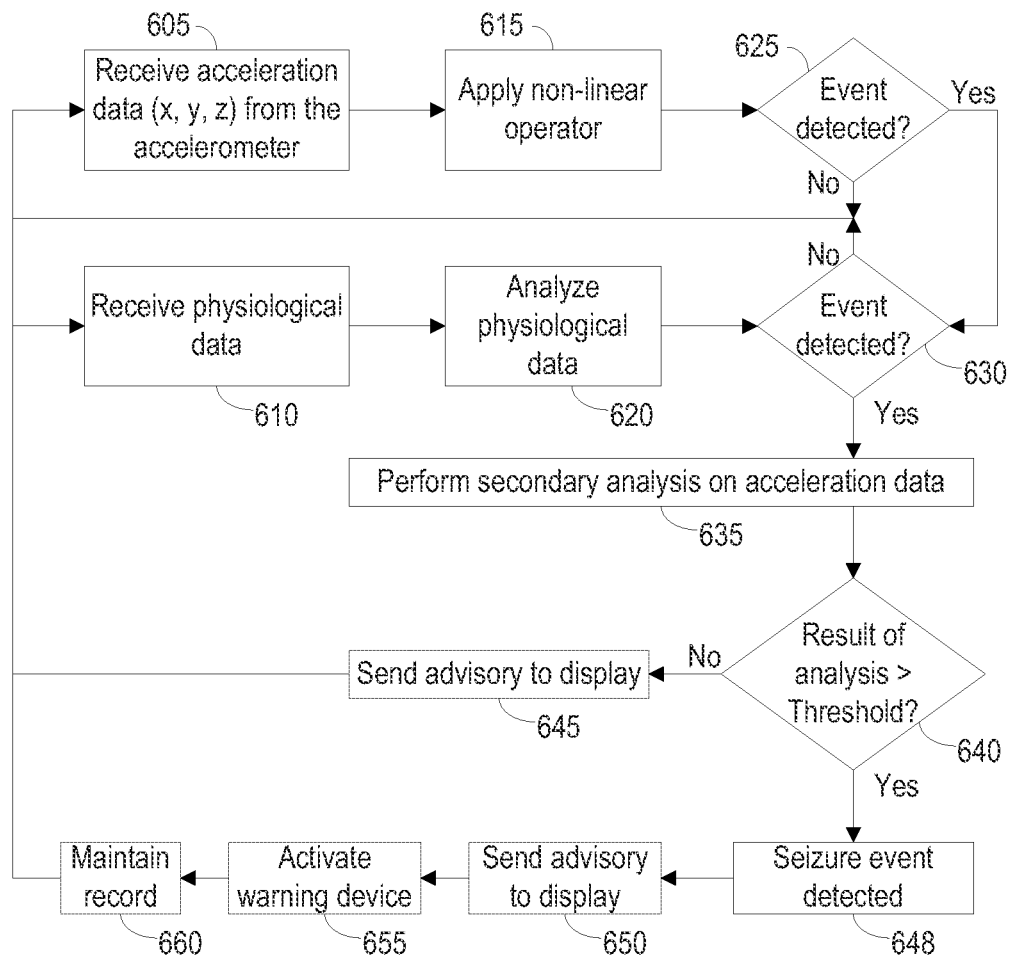
FIG. 6 is a flowchart of a seizure detection process in accordance with one or more embodiments of the present disclosure, using physiological data as well as accelerometer data.

FIG. 6 is a flowchart of a seizure detection process in accordance with one or more embodiments of the present disclosure, using physiological data as well as accelerometer data. The seizure detection process of FIG. 6 could be used, for example, with the seizure detection system 400 of FIG. 4. Acceleration data collected from an accelerometer on the patient's person may be received 605 at a processor. Physiological data such as, but not limited to, information about the patient's pulse, respiration, or EKG data from monitoring activity of the patient's heart may also be received 610 at the processor. The processor may be configured to apply a non-linear operator to the acceleration data, at 615, to determine whether the acceleration data indicates that an event has occurred at 625. If the acceleration data does not indicate an event has been detected, the process of receiving the acceleration data and the physiological data at the processor for analysis continues. The processor may be further configured to analyze the physiological data at 620, such as pulse rate and/or pulse strength and/or respiration, to determine whether the physiological data is indicative of an event occurring. If an event has been detected from the acceleration data, a determination is made 630 as to whether an event was also indicated by the physiological data. If the physiological data also supports a finding that an event has occurred, then secondary analysis of the acceleration data is performed 635 and the result compared 640 to a threshold. The secondary analysis could include measuring accelerometer dynamic activity and comparing it to a first predetermined threshold. Alternatively, the secondary analysis could include measuring the frequency domain features of the accelerometer data to determine a maximum frequency and comparing the maximum frequency to a second predetermined threshold. If the result of the secondary analysis is not greater than the threshold, an advisory that there has been a "Non-Seizure Event" may be sent 645 to the display. Acceleration data and physiological data may continue to be collected and received at the processor. If the result of the secondary analysis is greater than the appropriate threshold, the processor may be configured to detect a seizure event at 648. The processor may further be configured to send a "Seizure Event" advisory at 650 to the display and the warning device may be activated at 655. The warning device when activated could, for example, activate an alarm with a sound or a vibration. The warning device could also place a call with a recorded message, or send an e-mail or a text message, to one or more designated persons.

Continuing to refer to FIG. 6, the processor could maintain 660 a record, for example, of all seizure events, their onset, timing and/or duration, and noting the XL data or other measurements made at the time of the event. Alternatively, a record could be maintained by the processor for all events, not just seizure events. The record could be stored on the database in communication with the processor and could be sent to the display (or to secondary displays) for graphical or text display, either on demand or at periodic intervals. The record could also be downloaded onto one or more additional processors for convenience or further analysis.

Referring again to FIG. 6, returns to the input of the accelerometer data and the input of the EKG data at various points in the flowchart indicate that measurements preferably continue regardless of the findings of whether there is a seizure (unless, for example, the accelerometer or the physiological device is intentionally turned off).

In alternate embodiments of the present disclosure, a seizure is determined to have occurred when two of three indicators (accelerometer data, physiological data or secondary analysis) are indicative of a seizure. Less commonly, but for use with certain patients, the present disclosure could be set so that a seizure is determined to have occurred when one of the three indicators is indicative of a seizure. As mentioned above, in alternative embodiments of the present disclosure, if the EKG measurements contain too much noise, the processor could ignore the EKG measurements and focus only on one or more other measurements, such as accelerometer data or physiological data, for detection of seizures.

Figure 7A:
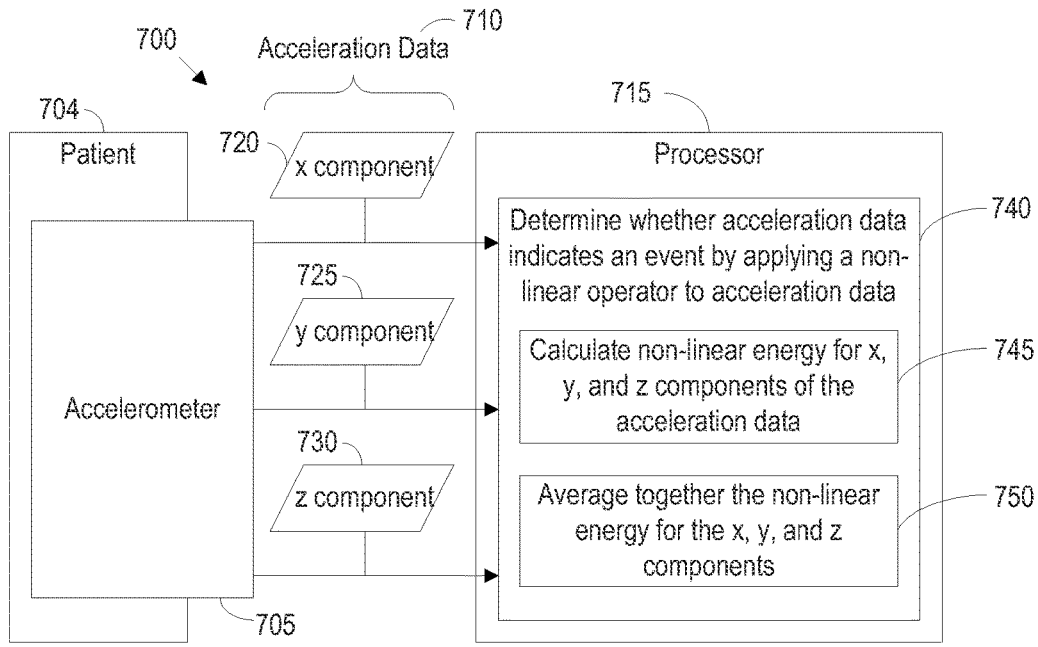
FIGS. 7A-B depict a schematic and flow diagram corresponding to a seizure detection device in accordance with an embodiment of the present disclosure, using x, y, and z components of accelerometer data.

FIG. 7A depicts a schematic of a seizure detection system 700 in accordance with one or more embodiments of the present disclosure. The seizure detection system 700 of may include an accelerometer 705 positioned on a patient 704 and a processor 715. The accelerometer 705 may be configured to provide acceleration data 710 to the processor 715. The acceleration data 710 may include an x component 720, a y component 725, and a z component 730. The processor 715 may be configured to determine, at 740, whether the acceleration data 710 indicates an event by applying a non-linear operator to the acceleration data 710. As part of the determining whether the acceleration data 710 indicates an event, the processor 715 may be further configured to calculate, at 745, the non-linear energy for the x, y, and z components of the acceleration data. Following the calculation, the processor 715 may be configured to average together the non-linear energy for the x, y, and z components. In addition, two or more accelerometers may be used on the patient 704. The additional accelerometers may be placed at other locations on the patient's body. For example, accelerometers may be placed on the patient's chest and one or more of the patient's limbs. An additional non-linear analysis may be performed for each additional accelerometer. The non-linear analyses may be performed simultaneously, in series, or an interleaved fashion.

Figure 7B:
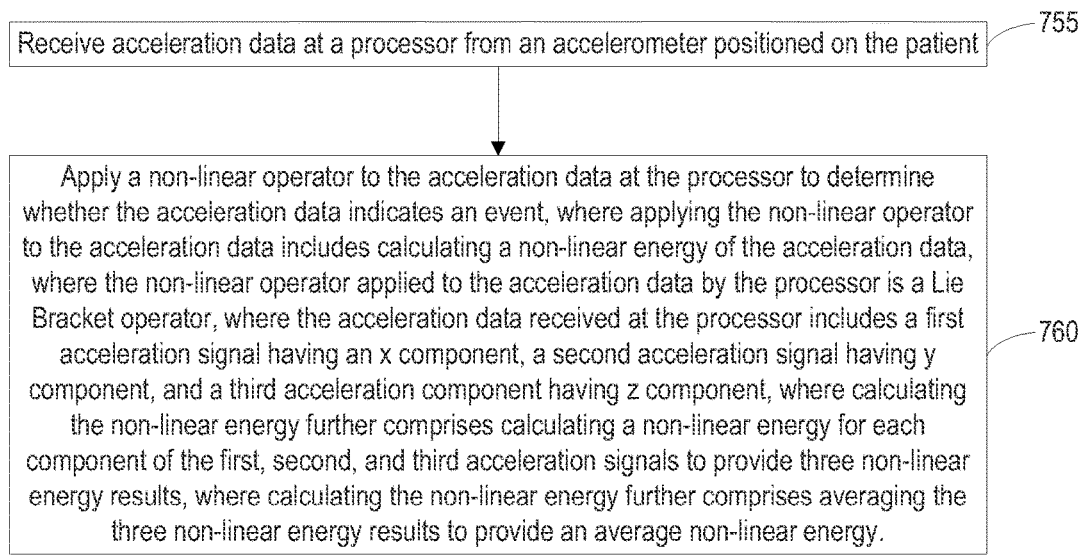
Figure 8:
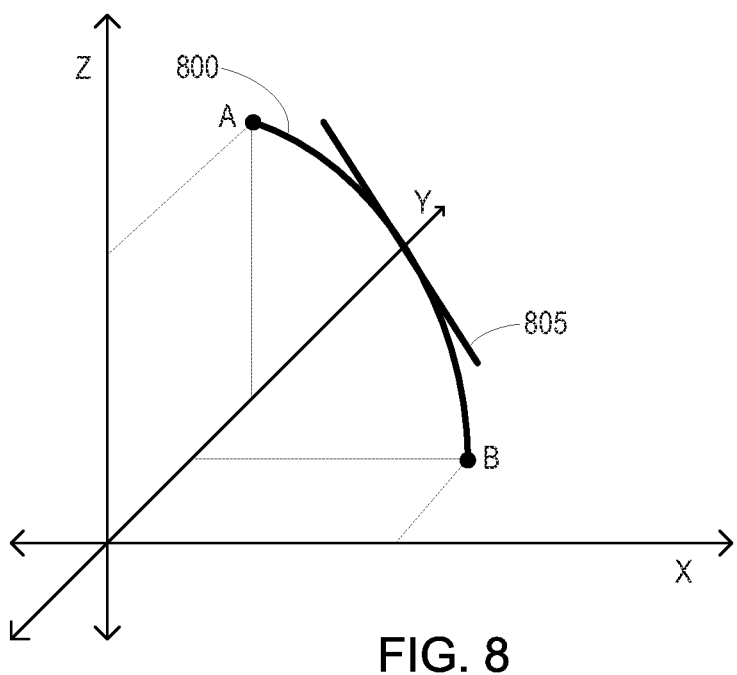
FIG. 8 is a graph depicting how movement of an accelerometer of the present disclosure worn on a patient's person might appear if plotted in three dimensions.

FIG. 7B is a flow diagram corresponding to a method of using a seizure detection device in accordance with one or more embodiments of the present disclosure. The processor receives acceleration data from an accelerometer positioned on the patient at 755. At 760, the processor applies a non-linear operator to the acceleration data to determine whether the acceleration data indicates an event. Applying the non-linear operator to the acceleration data includes calculating a non-linear energy of the acceleration data, where the non-linear operator applied to the acceleration data may be a Lie Bracket operator. The acceleration data received at the processor may include a first acceleration signal having an x component, a second acceleration signal having y component, and a third acceleration component having z component. Calculating the non-linear energy may include calculating a non-linear energy for each component of the first, second, and third acceleration signals to provide three non-linear energy results. Calculating the non-linear energy may further include averaging the three non-linear energy results to provide an average non-linear energy FIG. 8 is a graph depicting how movement of an accelerometer of the present disclosure worn on a patient's person might appear if plotted. If one moves in three dimensional space from point A to point B over a given time period, the resulting change in position may be plotted as a line or a curve 800 passing through three dimensions over time. In this case, the accelerometer starts with time equal to zero, at position A, at X=0, Y=2 and Z=3, such as might be true if a person were standing, with the accelerometer in a pocket. The accelerometer moves to position B, at X=3, Y=1 and Z=0, such as might occur if the person holding the accelerometer decided to lay down or sit on the ground (a slow operation, which might take five seconds) or fell down (a quick operation, which might take 1.5 seconds). Taking the derivative of the line or curve yields a tangent 805 to the line/curve at any particular point, which represents the speed at which the move was made at that particular point. Taking the derivative of the line/curve would yield a series of tangents, one at each point of the curve. Taking the second derivative of the line or curve (at any point), yields the slope of the tangent (at that point), which represents the acceleration (at that point). The acceleration will be greater if the person fell down rather than if the person lay down deliberately, and the slopes of the tangents will be greater. If one takes the slope of each of the series of tangents, one at every point along the curve, the slopes of the tangents will usually change with time, thus the acceleration will usually change with time.

The accelerometer of the present disclosure will preferably record the patient's proper acceleration "tri-axially." This means that the accelerometer will preferably record the proper acceleration in each of the three directions X, Y and Z, as the patient stands up, sits down, walks, jumps, runs, lies still, etc. Plotted as a function of time, the proper acceleration data is sent to the processor from the accelerometer as three curves or functions, one for acceleration in each direction, with each as a function of time.

As previously described herein with respect to FIGS. 1A-7B, when the proper acceleration data reaches the processor, the processor applies a non-linear operator, such as a Lie Bracket operator, to the proper application data. The non-linear operator (such as a Lie Bracket operator) will accentuate high amplitude (meaning large) changes in position and will accentuate frequent changes in position, which makes high amplitude and/or frequent changes in position stand out more clearly and easier to spot. This is important as seizures can result in high amplitude and/or frequent changes in position. To illustrate this, if a sinusoid curve, s=A sin (Ωt), where A is the amplitude of the sinusoid, t is time and Ω is the frequency of the sinusoid, then the energy of the sinusoid E is proportional to $A2$, while the non-linear energy, E (non-linear), of the same sinusoid curve, s, is proportional to $A2\ \Omega2$. This means changes in both the amplitude and the frequency may be detected more easily with the non-linear energy.

The equation for a Lie Bracket in continuous time is:

$$L[y,x] \equiv x'y - xy' \qquad \text{EQ. 1}$$

where L is the Lie Bracket of two functions y and x. The prime mark after the x and y indicates taking the derivative of the x and y with respect to time. (Two prime marks after an x, y, or z would indicate taking the second derivative.) Thus, to determine the Lie Bracket, L[y,x], one takes the derivative of x with respect to time, multiplied by y and subtracts from that the product of taking the derivative of y with respect to time multiplied by x.

The non-linear energy of the accelerometer data in the x direction, that is, of function x, such as acceleration in the x-direction, is denoted as Ψ(x):

$$\Psi(x) \equiv (x')2 - xx'' = L[x', x] \qquad \text{EQ. 2}$$

where Ψ(x) is defined as the derivative of x with respect to time, squared, minus the product of x multiplied by the second derivative of x with respect to time.

Different orders of Lie Bracket equations, where k represents the order and k=0, 1, 2, etc., may be:

$$\Gamma k(x) \equiv L[x(k-1), x] = x'x(k-1) - xx(k) \qquad \text{EQ. 3}$$

As one looks at higher order Lie Brackets—that is as "k" increases—more weight is given to changes in amplitude of the signal and less weight is given to changes in frequency of the signal. In some patients, the seizure may cause more frequent changes in position (and thus more frequent changes in the acceleration), while others may have seizures with higher amplitude changes of position. Thus, one might adjust the sensitivity of the Lie Bracket, by selecting a different order equation, to better fit with the type of seizures that a particular patient is experiencing.

A second order Lie Bracket equation (k=2) might be selected and used in some preferred embodiments of the present disclosure for typical patient cases. The second order Lie Bracket equation for energy of the accelerometer data in the x direction, in discrete time intervals "n", is Ψ(x[n]):

$$\Psi(x[n]) = x2[n] - x[n-1]*x[n+1] \qquad \text{EQ. 4}$$

As the data is coming from the accelerometer in three channels, one for acceleration in each direction x, y, and z, the processor of the present disclosure would apply Equation 4 (or another equation for a different order Lie Bracket equation) to the accelerometer data in each of three directions:

$$\Psi(x[n]) = x2[n] - x[n-1]*x[n+1] \qquad \text{EQ. 4, for x direction}$$

$$\Psi(y[n]) = y2[n] - y[n-1]*y[n+1] \qquad \text{EQ. 4 for y direction}$$

$$\Psi(z[n]) = z2[n] - z[n-1]*z[n+1] \qquad \text{EQ. 4 for z direction}$$

After calculating the energy Ψ for proper acceleration in each direction, the processor may average the three values of Ψ (one for each direction) to obtain an average Ψ. The average Ψ could be used to determine whether an event has occurred, as in, for example, at 210 of FIG. 2, at 310 of FIG. 3, at 525 of FIG. 5, or at 625 of FIG. 6. A greater non-linear energy of acceleration means a higher likelihood of a seizure or other event (such as a non-seizure related fall).

Figure 9:
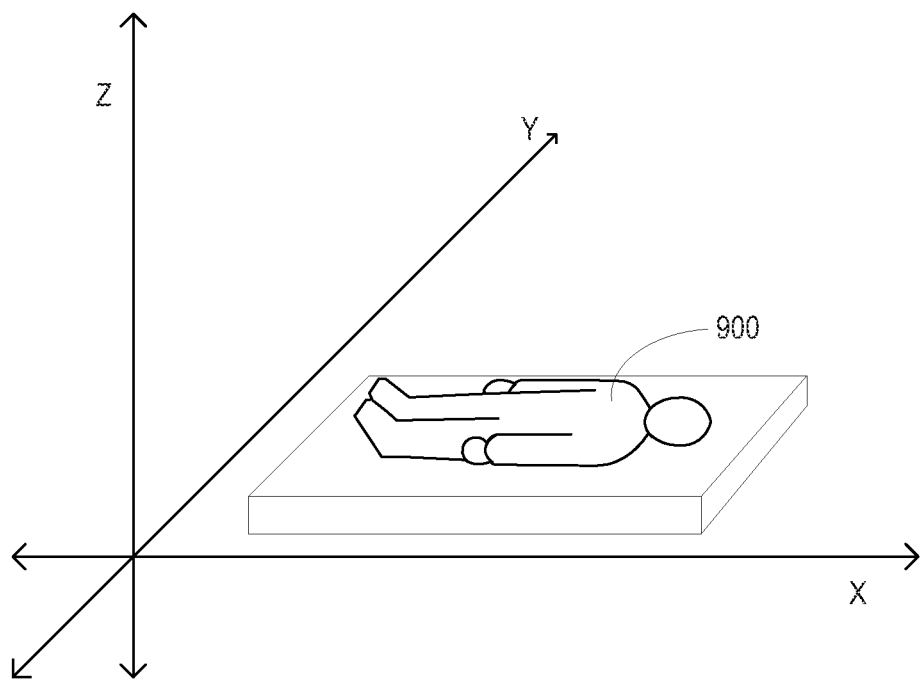
FIG. 9 depicts a person in a sleeping position, with the X, Y and Z directions marked.

But in some embodiments of the present disclosure, the processor may perform comparisons between the values of Ψ obtained for the different directions or focus on values of Ψ obtained for specific directions. For example, the processor could be set to a special mode when the patient is asleep. FIG. 9 depicts a person 900 in a sleeping position, with the X, Y and Z directions marked. The X direction is along the length of the bed, the Y direction is along the width of the bed and the Z direction is up from the bed (which would appear to be coming out of the paper towards the viewer). As the person 900 turns normally during sleep, the person is likely to make gentle moves in the Y direction and, perhaps small movements in the Z direction. The processor could focus on these directions and look at the X direction more closely if the movements in the Y and Z directions increase in frequency and/or amplitude. In addition, examining the three values of Ψ obtained for the three different directions might give some indication of the type or severity of seizures experienced by a particular patient.

Figure 10A:
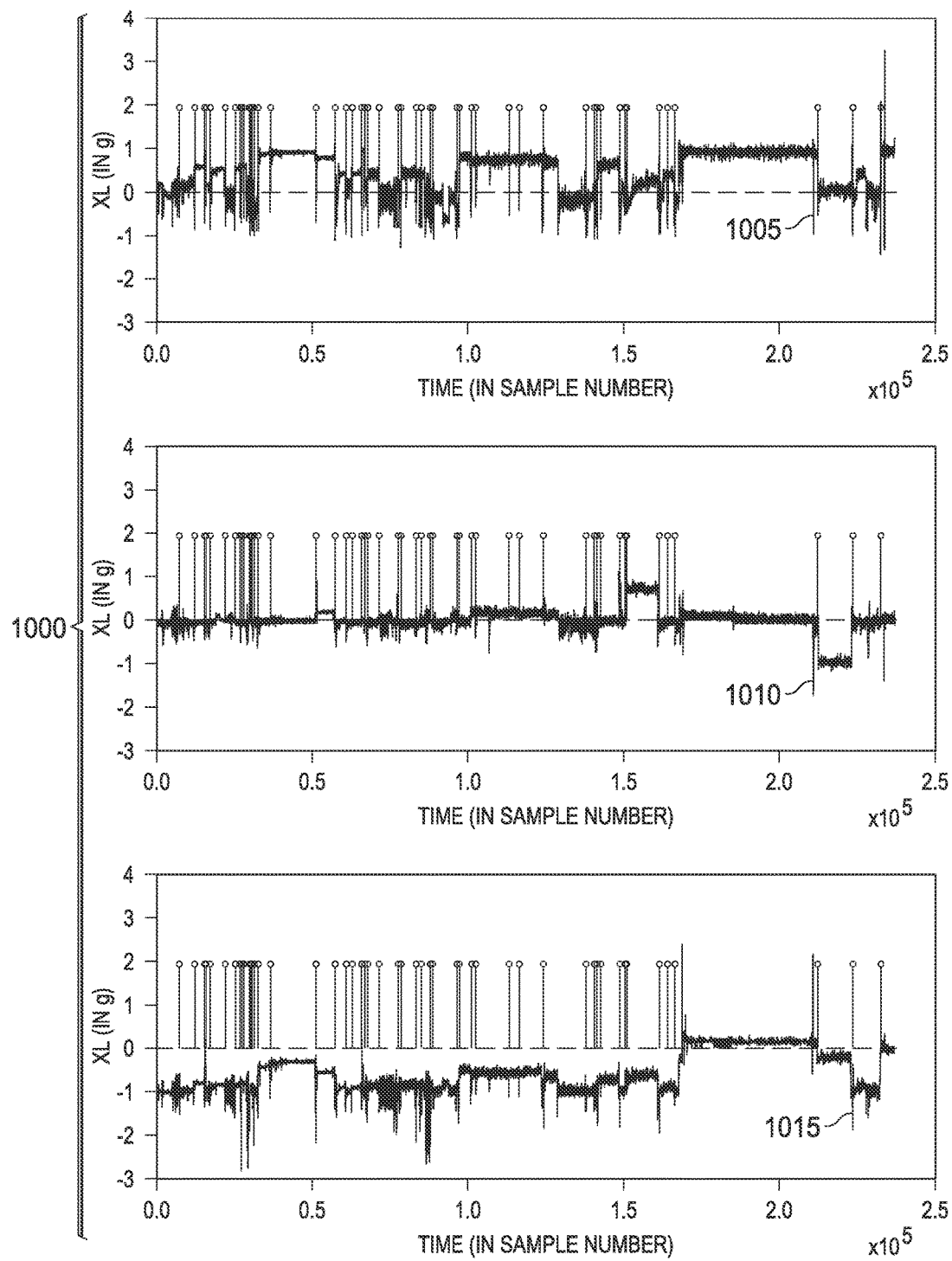

FIG. 10A depicts an example of three channels of accelerometer data 1000 as sent from the accelerometer to the processor with accelerometer data in the X direction 1005, accelerometer data in the Y direction 1010, and accelerometer data 1015 in the Z direction. The markers displayed on the graph represent changes, or spikes, in the accelerometer data that exceeds a threshold. FIG. 10B is an expanded version 1020 of a portion of FIG. 10A.

FIG. 11 depicts a waveform 1100 of the average non-liner energy Ψ of the same three channels of accelerometer data 1005, 1010, and 1015 of FIGS. 10A-B. In other words, a second order Lie Bracket equation has been applied to the data from each of the three channels of FIGS. 10A-B to calculate the non-linear energy of each (Ψ(x[n]), Ψ(y[n]), and Ψ(z[n])), with the results averaged to get an average Ψ. Spikes in the average non-liner energy Ψ are more easily recognized in FIG. 11, than spikes in the data of FIGS. 10A and 10B, leading to easier detection of seizures. Line 1105 represents a threshold that can be set to detect spikes exceeding an energy level. The threshold may be modified to adjust the sensitivity of the spike detection. For example, a threshold set to a non-linear energy value of 10 would detect fewer spikes than a threshold set to a non-linear energy value 2.

In some embodiments, multiple thresholds may also be used to detect spikes within predefined energy ranges. Larger spikes, or spikes in higher energy ranges, may be more indicative of a seizure event; however, it may still be beneficial to detect smaller spikes, or spikes in lower energy ranges, as these may be indicative of seizure events, or particular phases of a seizure event. Using multiple thresholds may increase the granularity of the spike and seizure detection. The multiple thresholds may be used to train a spike and/or seizure detection algorithm to a particular patient's seizure signature to improve detection accuracy.

In light of the principles and example embodiments described and illustrated herein, it will be recognized that the example embodiments can be modified in arrangement and detail without departing from such principles. Also, the foregoing discussion has focused on particular embodiments, but other configurations are contemplated. In particular, even though expressions such as "in one embodiment," "in another embodiment," or the like are used herein, these phrases are meant to generally reference embodiment possibilities, and are not intended to limit the disclosure to particular embodiment configurations. As used herein, these terms may reference the same or different embodiments that are combinable into other embodiments.

Similarly, although example processes have been described with regard to particular operations performed in a particular sequence, numerous modifications could be applied to those processes to derive numerous alternative embodiments of the present disclosure. For example, alternative embodiments may include processes that use fewer than all of the disclosed operations, processes that use additional operations, and processes in which the individual operations disclosed herein are combined, subdivided, rearranged, or otherwise altered.

This disclosure also described various benefits and advantages that may be provided by various embodiments. One, some, all, or different benefits or advantages may be provided by different embodiments.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A system comprising:
   at least one accelerometer configured to be positioned on a patient, the at least one accelerometer configured to generate acceleration data;
   a processor in communication with the at least one accelerometer, the processor configured to:
      receive acceleration data from the at least one accelerometer;
      determine a plurality of components of the acceleration data;
      calculate, for each of the plurality of components, a non-linear energy of the component by applying one or more non-linear operators to the component;
      calculate a non-linear energy of the acceleration data by combining the non-linear energies of the plurality of components of the acceleration data;
      perform a first comparison of the non-linear energy of the acceleration data to a first threshold;
      determine, based on the first comparison, whether the nonlinear energy of the acceleration data indicates an event; and
      if the non-linear energy indicates the event:
         perform a second comparison of the acceleration data to a second threshold; and
         determine, based on the second comparison, whether the event is a seizure; and
   a warning device that activates an alarm in response to receiving an indication from the processor that the event is a seizure.

2. The system of claim 1, further comprising:
   a database configured to maintain a record of one or more events.

3. The system of claim 1, wherein the at least one accelerometer includes a first accelerometer and a second accelerometer, wherein the first accelerometer and the second accelerometer are positioned at different locations on the patient.

4. The system of claim 1, wherein the plurality of components of the acceleration data include a dynamic activity of the acceleration data, and wherein the second threshold includes a dynamic activity threshold.

5. The system of claim 1, wherein the plurality of components of the acceleration data include frequency domain features of the acceleration data, and wherein the second threshold includes a frequency threshold.

6. The system of claim 1, wherein at least one of the non-linear operators applied to the acceleration data by the processor is a Lie Bracket operator.

7. The system of claim 6, wherein the acceleration data includes a first acceleration component having an x component, a second acceleration component having a y component, and a third acceleration component having a z component.

8. The system of claim 7, wherein the non-linear energy is determined by calculating a non-linear energy for each component of the first, second, and third acceleration components to provide three results and averaging the three results together to calculate the non-linear energy.

9. The system of claim 1, further comprising:
one or more physiological monitoring systems for collecting one or more physiological measurements of the patient, the one or more physiological monitoring systems that send the one or more physiological measurements to the processor, wherein the processor analyzes the one or more physiological measurements to determine whether the one or more physiological measurements support a determination that the event is a seizure.

10. The system of claim 9, wherein the one or more physiological monitoring systems includes an EKG monitoring system that collects EKG measurements from the patient.

11. The system of claim 10, wherein the EKG monitoring system analyzes the EKG measurements to determine whether the EKG measurements support a determination that the event is a seizure, wherein the determination is based on a use of a relative heart rate detection algorithm.

12. The system of claim 11, wherein the EKG monitoring system performs a noise analysis, wherein the EKG measurements are disregarded to determine whether the event is a seizure when the noise analysis determines that a level of noise in the EKG measurements is too high.

13. The system of claim 9, wherein the one or more physiological monitoring systems includes one or more of a respiration monitoring system, or a skin resistivity monitoring system.

14. An apparatus comprising:
at least one accelerometer configured to be positioned on a patient, the at least one accelerometer configured to generate acceleration data;
a processor in configured to communicate with the at least one accelerometer and configured to:
receive the acceleration data from the at least one accelerometer;
determine a first dimension, a second dimension and a third dimension of the acceleration data;
calculate a first non-linear energy of the first dimension of the acceleration data by applying a first non-linear operator to the first dimension of the acceleration data;
calculate a second non-linear energy of the second dimension of the acceleration data by applying a second non-linear operator to the second dimension of the acceleration data:
calculate a third non-linear energy of the third dimension of the acceleration data by applying a third non-linear operator to the third dimension of the acceleration data;
calculate a non-linear energy of the acceleration data by combining the first non-linear energy, the second non-linear energy, and the third non-linear energy of the acceleration data;
perform a first comparison of the non-linear energy of the acceleration data to a first threshold to determine whether the non-linear energy of the acceleration data indicates an event; and
if the non-linear energy indicates the event;
perform a second comparison of the acceleration data to a second threshold; and
determine, based on the second comparison, whether the event is a seizure; and
a warning device that activates an alarm in response to receiving an indication from the processor that the event is a seizure.

15. The apparatus of claim 14, further comprising a memory to store settings to indicate when the patient is engaged in different levels of activity, wherein the levels of activity include strenuous activity, normal activity, sedentary activity or sleeping activity.

16. A method, comprising:
receiving acceleration data at a processor from at least one accelerometer positioned on a patient;
determining a plurality of components of the acceleration data;
calculating, for each of the plurality of components, a non-linear energy of the components by applying a non-linear operator to the component at the processor;
calculating a non-linear energy of the acceleration data by combining the non-linear energies of the components of the acceleration data;
performing a first comparison of the non-linear energy of the acceleration data to a first threshold;
determining, based on the first comparison, whether the non-linear energy of the acceleration data indicates an event;
if the non-linear energy indicates the event:
performing a second comparison of the acceleration data to a second threshold;
determining, based on the second comparison, whether the event is a seizure; and
activating an alarm on a warning device in response to determining the event is a seizure.

17. The method of claim 16, wherein performing the second comparison of the acceleration data to the second threshold further comprises:
measuring frequency domain features of the acceleration data to determine a maximum frequency; and
comparing the maximum frequency to the second threshold.

18. The method of claim 16, further comprising:
maintaining a record in a database of one or more events.

19. The method of claim 16, wherein the plurality of components of the acceleration data include dynamic activity of the acceleration data and, wherein the second threshold includes a dynamic activity threshold.

20. The method of claim 16, wherein the plurality of components of the acceleration data include frequency domain features of the acceleration data, and wherein the second threshold includes a frequency threshold.

21. The method of claim 16, wherein the non-linear operator applied to the acceleration data by the processor is a Lie Bracket operator.

22. The method of claim 21, wherein application of the Lie Bracket operator to the acceleration data includes use of a second order Lie Bracket equation.

23. The method of claim 21, wherein the acceleration data received at the processor includes a first acceleration component having an x component, a second acceleration component having a y component, and a third acceleration component having a z component.

24. The method of claim 23, wherein calculating the non-linear energy further comprises calculating a non-linear energy for each component of the first, second, and third acceleration components to provide three results and averaging the three results to provide the non-linear energy.

25. The method of claim 16, further comprising sending an activation signal to a warning device in response to determining that the event is a seizure.

26. The method of claim 25, wherein the warning device is configured to electrically stimulate a cranial nerve or brain tissue in response to the activation signal.

* * * * *